(12) United States Patent
Buehler et al.

(10) Patent No.: US 8,871,779 B2
(45) Date of Patent: Oct. 28, 2014

(54) PROCESS FOR PREPARING MORPHINAN-6-ONE PRODUCTS WITH LOW LEVELS OF α,β-UNSATURATED KETONE COMPOUNDS

(75) Inventors: Henry J. Buehler, St. Louis, MO (US); William E. Dummitt, St. Louis, MO (US); Anthony Mannino, Maryland Heights, MO (US); Dennis C. Aubuchon, Arnold, MO (US); Hong Gu, Oak Park, CA (US)

(73) Assignee: Mallinckrodt LLC, Hazelwood, MO (US)

( * ) Notice: Subject to any disclaimer, the term of this patent is extended or adjusted under 35 U.S.C. 154(b) by 996 days.

(21) Appl. No.: 11/915,606

(22) PCT Filed: Mar. 2, 2007

(86) PCT No.: PCT/US2007/005256
§ 371 (c)(1),
(2), (4) Date: Nov. 27, 2007

(87) PCT Pub. No.: WO2007/103105
PCT Pub. Date: Sep. 13, 2007

(65) Prior Publication Data
US 2008/0312442 A1     Dec. 18, 2008

Related U.S. Application Data

(60) Provisional application No. 60/778,258, filed on Mar. 2, 2006.

(51) Int. Cl.
*A61K 31/485* (2006.01)
*C07D 489/04* (2006.01)
*C07D 489/08* (2006.01)

(52) U.S. Cl.
CPC .................. *C07D 489/08* (2013.01)
USPC ............................. 514/282; 546/45

(58) Field of Classification Search
USPC ...................... 546/45, 44; 514/282
See application file for complete search history.

(56) References Cited

U.S. PATENT DOCUMENTS

| | | |
|---|---|---|
| 1,479,293 A | 1/1924 | Freund |
| 2,009,181 A | 7/1935 | Kabay |
| 4,368,326 A | 1/1983 | Rice |
| 4,410,700 A | 10/1983 | Rice |
| 4,414,417 A | 11/1983 | Mestroni et al. |
| 4,435,572 A | 3/1984 | Rapoport et al. |
| 4,467,112 A | 8/1984 | Matsuura et al. |
| 4,521,601 A | 6/1985 | Rice |
| 4,556,712 A | 12/1985 | Rice |
| 4,613,668 A | 9/1986 | Rice |
| 4,727,146 A | 2/1988 | Rice |
| 5,869,669 A | 2/1999 | Huang |
| 5,922,876 A | 7/1999 | Huang |
| 6,008,355 A | 12/1999 | Huang et al. |
| 6,046,185 A | 4/2000 | Burgoyne et al. |
| 6,177,567 B1 | 1/2001 | Chiu et al. |
| 6,312,662 B1 | 11/2001 | Erion et al. |

(Continued)

FOREIGN PATENT DOCUMENTS

| | | |
|---|---|---|
| EP | 0 604 150 | 6/1994 |
| FR | 1000543 | 2/1952 |

(Continued)

OTHER PUBLICATIONS

Weiss, "Derivatives of Morphine. I. 14-Hydroxydihydromorphinone", Journal of the American Chemical Society, Nov. 20, 1955, pp. 5891-5892.

(Continued)

*Primary Examiner* — Charanjit Aulakh
(74) *Attorney, Agent, or Firm* — Buchanan Ingersoll & Rooney PC

(57) ABSTRACT

The present invention generally relates to processes for preparing highly pure morphinan-6-one products. The processes involve reducing the concentration of α,β-unsaturated ketone compounds present as impurities in morphinan 6 one products or reaction mixtures including morphinan 6 one compounds by treatment with a sulfur-containing compound. (A)

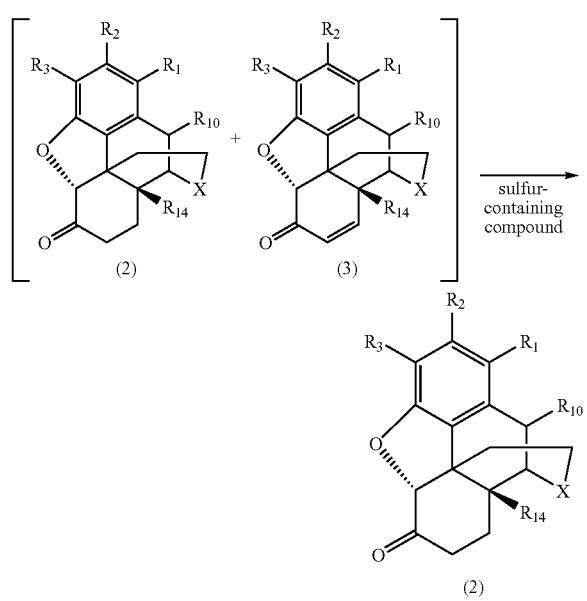

6 Claims, No Drawings

(56) References Cited

U.S. PATENT DOCUMENTS

| | | | |
|---|---|---|---|
| 6,482,959 | B1 | 11/2002 | Baloghne et al. |
| 7,129,248 | B2 * | 10/2006 | Chapman et al. ............. 514/282 |
| 7,851,482 | B2 | 12/2010 | Dung |
| 8,134,002 | B2 | 3/2012 | Huang |
| 8,217,175 | B2 | 7/2012 | Wang |
| 8,227,609 | B2 | 7/2012 | Weigl |
| 2002/0052345 | A1 | 5/2002 | Erion et al. |
| 2005/0222188 | A1 | 10/2005 | Chapman |
| 2008/0146601 | A1 | 6/2008 | Sun |

FOREIGN PATENT DOCUMENTS

| | | |
|---|---|---|
| GB | 713689 | 8/1954 |
| JP | 60193902 | 10/1985 |
| WO | WO 80/00841 | 5/1980 |
| WO | WO 97/22602 | 6/1997 |
| WO | WO 2005/097801 | 10/2005 |
| WO | WO 2006/084389 | 8/2006 |
| WO | WO 2006/084412 | 8/2006 |
| WO | WO 2006/094672 | 9/2006 |
| WO | WO 2007/103105 A2 | 9/2007 |

OTHER PUBLICATIONS

Findlay, "The Three-Dimensional Structures of the Cocaines. II. Racemic Allococaine and Racemic Allopseudococaine", Journal of the American Chemical Society, vol. 24, Oct. 1959, pp. 1540-1550.
Gassman et al., "Mechanism of Sodium Dithionite Reduction of Aldehydes and Ketones", J. Org. Chem. , 1981, 46, pp. 5457-5458.
Dhillon et al., "Selective 1,4-Reduction of conjugated Aldehydes and Ketones in the Presence of Unconjugated Aldehydes and Ketones with Sodium Dithionite", T. Letters, 36, 7, 1995, pp. 1107-1108.
Iijima et al., "Studies in the (+)-morphinan series. 5. Synthesis and biological properties of (+)-Naloxone", Journal of Medicinal Chemistry, v. 21, 1978, pp. 398-400, XP002446243.
Rapoport et al., "The Synthesis of thebaine and Northebaine from Codeinone Dimethyl Ketal", Journal of the American Chemical Society, 89:8, Apr. 1967, pp. 1942-1947.
Camps et al., "A Two Step Procedure as Improved Alternative to the cyclocarbonylation of Allyl Halides and Acetylene Derivatives Mediated by $Ni(CO)_4$", Tetrahedron Letters, vol. 29, No. 45, 1988, pp. 5811-5814.
Louis-Andre et al., "Exclusive 1-4 Reduction of conjugated Ketones by Sodium Dithinite", Tetrahedron Letters, vol. 26, No. 7, 1985, pp. 831-832.
March, J., "Addition to Carbon-Carbon Multiple Bonds", Advanced Organic Chemistry, J. Wiley & Sons, 1985, 3d Ed., pp. 686-691.
Gilbert, E., Sulfonation and Related Reactions, Interscience, NY, 1965, pp. 125-199.
Patai et al., The Chemistry of Alkenes, Interscience, London, 1965, p. 478.
Barbier, "The Extraction of Opium, Twenty-five years of commercial experience in the treatment of opium", Ann. Pharm. Franc., 1947, 5, 121-140.
Barbier, "The Extraction of Opium Alkaloids", Bull. Narcotics, 1950, vol. 3, pp. 22-29.
Heumann, "The manufacture of alkaloids from opium", Bull Narcotics, 1957, vol. 2, pp. 34-40.
Lednicer & Mitscher, Organic Chemistry of Drug Synthesis, Ch. 15, (Wiley 1977).
Bentley, "XVII. 14-Hydroxycodeinone, 14-Bromocodeinone, and Their Derivatives", The Chemistry of the Morphine Alkaloids. 1954, pp. 251-254, 262.
Communication of a notice of opposition, Application No. 07751984.1-2117/1994024, European Patent Office, Aug. 23, 2010.
Buehler Motion 2 (for judgment based on priority), filed on May 16, 2013 in Interference No. 105,893.
Dung Opposition 2, filed on Jul. 23, 2013 in Interference No. 105,893.
Buehler Reply 2, filed on Aug. 30, 2013 in Interference No. 105,893.
Dung Motion 1 (Buehler's claims are not supported under 35 U.S.C. 112, first paragraph), filed Feb. 19, 2013 in Interference No. 105,893.
Buehler Opposition 1, filed Jul. 23, 2013 in Interference No. 105,893.
Dung Reply 1, filed Aug. 30, 2013 in Interference No. 105,893.
Dung Motion 2 (for judgment based on priority), filed Feb. 19, 2013 in Interference No. 105,893.
Buehler Opposition 2, filed Jul. 23, 2013 in Interference No. 105,893.
Dung Reply 2, filed Aug. 30, 2013 in Interference No. 105,893.
Judgment filed Dec. 19, 2013 (Paper 293) in Interference No. 105,893.
M. P. Adams and H. Ahdieh, "Pharmacokinetics and Dose-Proportionality of Oxymorphone Extended Release and Its Metabolites: Results of a Randomized Crossover Study," Pharmacotherapy, 24(4):468-476 (2004) (Exhibit 1039, filed in Interference No. 105,893).
W. T. Beaver et al., "Comparisons of the Analgesic Effects of Oral and Intramuscular Oxymorphone and of Intramuscular Oxymorphone and Morphine in Patients with Cancer," The Journal of Clinical Pharmacology, 17:186-198 (1977) (Exhibit 1040, filed in Interference No. 105,893).
U.S. Appl. No. 11/915,606, filed Nov. 27, 2007, which is a U.S. national stage of International PCT Application No. PCT/US07/05256, filed on Mar. 2, 2007 (Exhibit 1041, filed in Interference No. 105,893).
Excerpts from Laboratory Notebook No. 5266 (pp. 106-108), issued to Hong Gu, 2003 (Exhibit 1042, filed in Interference No. 105,893).
Declaration of Dennis Aubuchon, dated May 13, 2013 (Exhibit 1043, filed in Interference No. 105,893).
Excerpts from Laboratory Notebook No. 5985 (pp. 6, 15-17, 19, 33-35, 43-48, 127, 140, 141), issued to Dennis Aubuchon on Mar. 5, 2004 (Exhibit 1044, filed in Interference No. 105,893).
Excerpts from Laboratory Notebook 6254 (pp. 104-108, 153, 154, 159-161, 168, 169), issued to Sharon Woods on Sep. 10, 2004 (Exhibit 1045, filed in Interference No. 105,893).
Excerpts from Laboratory Notebook 5981 (pp. 60-63, 84-96, 153-156), issued to Larry Snopek on Feb. 23, 2004 (Exhibit 1046, filed in Interference No. 105,893).
Declaration of Edward S. Yeung, Ph.D., dated May 16, 2013 (Exhibit 1047, filed in Interference No. 105,893).
Photograph of bottle labeled "sodium hydrosulfite" with Code 7672, Lot KTLA, 2013 (Exhibit 1048 filed in Interference No. 105,893).
Declaration of William Dummitt, dated May 14, 2013 (Exhibit 1049, filed in Interference No. 105,893).
*Curriculum Vitae* of Edward S. Yeung, Ph.D., 2013 (Exhibit 1050, filed in Interference No. 105,893).
Diane Allen's Monthly Report for Feb. 2005 with redactions (Exhibit 1051, filed in Interference No. 105,893).
William Dummitt's Monthly Report for Jul./Aug. 2005 with redactions, dated Sep. 2, 2005 (Exhibt 1052, filed in Interference No. 105,893).
PCT International Publication No. WO 80/00841, published on May 1, 1980 (Exhibit 1053, filed in Interference No. 105,893).
Declaration of Diane Allen, dated May 15, 2013 (Exhibit 1054, filed in Interference No. 105,893).
Excerpts from Laboratory Notebook 5588 (pp. 38, 39, 42, 47, 139), issued to Henry Buehler, 2003 (Exhibit 1055, filed in Interference No. 105,893).
Excerpts from Laboratory Notebook 5717 (pp. 22, 23, 25, 26, 67, 68, 70, 71, 78, 79, 81-83, 85-91, 186-189), issued to Diane Allen, 2003-2005 (Exhibit 1056, filed in Interference No. 105,893).
Diane Allen's Monthly Report for Mar. 2004 with redactions (Exhibit 1057, filed in Interference No. 105,893).
Excerpts from Laboratory Notebook 6660 (pp. 30-32, 83-86), issued to Larry Snopek, 2005 (Exhibit 1058, filed in Interference No. 105,893).
Excerpts from Laboratory Notebook 6548 (pp. 6, 27-31, 58, 62-64), issued to Diane Allen, 2005 (Exhibit 1059, filed in Interference No. 105,893).
Declaration of Anthony Mannino, dated May 13, 2013 (Exhibit 1060, filed in Interference No. 105,893).
Excerpts from Laboratory Notebook 7463 (pp. 175, 176, 180), issued to Steven Bryant, 2006 (Exhibit 1062, filed in Interference No. 105,893).

(56) References Cited

OTHER PUBLICATIONS

Excerpts from Laboratory Notebook 5187 (p. 124), issued to Pamela Utrecht, 2002 (Exhibit 1063, filed in Interference No. 105,893).
Declaration of Henry J. Buehler, dated May 15, 2013 (Exhibit 1064, filed in Interference No. 105,893).
Declaration of Lawrence Snopek, dated May 15, 2013 (Exhibit 1065, filed in Interference No. 105,893).
Lawrence Snopek's Monthly Report for Apr. 2003 with redactions (Exhibit 1066, filed in Interference No. 105,893).
Lawrence Snopek's Monthly Report for May 2003 with redactions (Exhibit 1067, filed in Interference No. 105,893).
Lawrence Snopek's Monthly Report for Jun. 2003 with redactions (Exhibit 1068, filed in Interference No. 105,893).
Declaration of Sharon Woods, dated May 13, 2013 (Exhibit 1069, filed in Interference No. 105,893).
Declaration of Steven Bryant, dated May 13, 2013 (Exhibit 1070, filed in Interference No. 105,893).
Lawrence Snopek's Monthly Report for Jul. 2003 with redactions (Exhibit 1071, filed in Interference No. 105,893).
Excerpts from Laboratory Notebook 5446 (pp. 74-77, 185-187), issued to Lawrence Snopek, 2003-2004 (Exhibit 1072, filed in Interference No. 105,893).
Chromatograms showing results of injections conducted by Sharon Woods on Jan. 28, 2005 printed on Feb. 1, 2005 (Exhibit 1073, filed in Interference No. 105,893).
Chromatograms showing results of injections started by Sharon Woods on Jan. 31, 2005 reprinted on Apr. 25, 2013 (Exhibit 1074, filed in Interference No. 105,893).
Chromatograms showing results of injections started by Sharon Woods on Jan. 28, 2005 reprinted on Apr. 25, 2013 (Exhibit 1075, filed in Interference No. 105,893).
Deposition Transcript of Erno Keskeny, Ph.D., May 7, 2013 (Exhibit 1076, filed in Interference No. 105,893).
Deposition Transcript of Edward S. Yeung, Ph.D., Jun. 5, 2013, with Errata Sheet (Exhibit 1077, filed in Interference No. 105,893).
Deposition Transcript of Dr. Peter A. Crooks, May 30, 2013 (Exhibit 1078, filed in Interference No. 105,893).
Deposition Transcript of Timothy Davies, Ph.D., May 1, 2013 (Exhibit 1079, filed in Interference No. 105,893).
Deposition Transcript of Nicolas Archer, Ph.D., May 3, 2013 (Exhibit 1080, filed in Interference No. 105,893).
*Bai v. Laiko*, Patent Interference No. 104,745, Paper 139 (B.P.A.I. 2004) (Exhibit 1081, filed in Interference No. 105,893).
*Brake v. Singh*, Patent Interference 102,728, Paper 199 (B.P.A.I. 2001) (Exhibit 1082, filed in Interference No. 105,893).
*Stice v. Campbell*, Patent Interference No. 104,746, Paper 123 (B.P.A.I. 2004) (Exhibit 1083, filed in Interference No. 105,893).
*Geerts v. Sugano*, Patent Interference No. 104,132, Paper 74 (B.P.A.I. 2001) (Exhibit 1084, filed in Interference No. 105,893).
Declaration of Stephen M. Husbands, Ph.D., dated Jul. 17, 2013 (Exhibit 1085, filed in Interference No. 105,893).
*Curriculum Vitae* of Stephen M. Husbands, Ph.D., 2013 (Exhibit 1086, filed in Interference No. 105,893).
Declaration of James W. Janetka, Ph.D., dated Jul. 16, 2013 (Exhibit 1087, filed in Interference No. 105,893).
*Curriculum Vitae* of James W. Janetka, Ph.D., 2013 (Exhibit 1088, filed in Interference No. 105,893).
HPLC-UV Chromatographic Data Obtained Jul. 1, 2013 (Exhibit 1089, filed in Interference No. 105,893).
HPLC-MS Chromatographic Data Obtained Jun. 20, 2013 (Exhibit 1090, filed in Interference No. 105,893).
Deposition Transcript of Stephen Husbands, Ph.D., Aug. 14, 2013, with Errata Sheet (Exhibit 1091, filed in Interference No. 105,893).
Deposition Transcript of James Janetka, Ph.D., Aug. 14, 2013 (Exhibit 1092, filed in Interference No. 105,893).
Declaration of Peter A. Crooks, Ph.D., dated Feb. 18, 2013 (Exhibit 2001, filed in Interference No. 105,893).
Curriculum vitae of Peter A. Crooks, Ph.D., dated Oct. 2012 (Exhibit 2002, filed in Interference No. 105,893).

U.S. Patent No. 7,851,482, issued on Dec. 14, 2010 (Exhibit 2003, filed in Interference No. 105,893).
U.S. Appl. No. 11/866,840, filed Oct. 3, 2007 (Exhibit 2004, filed in Interference No. 105,893).
U.S Patent Publication 2008/0146601 on Jun. 19, 2008 (Exhibit 2005, filed in Interference No. 105,893).
U.S. Publication No. 2008/0312442 on Dec. 18, 2008 (Exhibit 2006, filed in Interference No. 105,893).
PCT/US07/05256, filed on Mar. 2, 2007 (Exhibit 2007, filed in Interference No. 105,893).
WO 2007/103105 on Sep. 13, 2007 (Exhibit 2008, filed in Interference No. 105,893).
U.S. Appl. No. 60/778,258, filed Mar. 2, 2006 (Exhibit 2009, filed in Interference No. 105,893).
Laboratory Notebook # 2130 of Dr. Jen-Sen Dung, dated Sep. 12, 2005 (Exhibit 2010, filed in Interference No. 105,893).
Laboratory Notebook # 2186 of Dr. Jen-Sen Dung, dated May 16, 2006 (Exhibit 2011, filed in Interference No. 105,893).
Laboratory Notebook # 2187 of Dr. Jen-Sen Dung, dated Mar. 13, 2007 (Exhibit 2012, filed in Interference No. 105,893).
Progress Report for May 2005 from Erno Keskeny, dated Jun. 2, 2005 (Exhibit 2013, filed in Interference No. 105,893).
Progress Report for Jun. 2005 from Erno Keskeny, dated Jun. 27, 2005 (Exhibit 2014, filed in Interference No. 105,893).
Progress Report for Jul. 2005 from Erno Keskeny, dated Jul. 27, 2005 (Exhibit 2015, filed in Interference No. 105,893).
Progress Report for Jul. 2005 from Jen-Sen Dung, dated Jul. 28, 2005 (Exhibit 2016, filed in Interference No. 105,893).
Progress Report for Aug. 2005 from Erno Keskeny, dated Aug. 31, 2005 (Exhibit 2017, filed in Interference No. 105,893).
Progress Report for Nov. 2005 from Erno Keskeny, dated Dec. 1, 2005 (Exhibit 2018, filed in Interference No. 105,893).
Monthly Report for Nov. 2005 from Jen-Sen Dung, dated Dec. 1, 2005 (Exhibit 2019, filed in Interference No. 105,893).
Progress Report for Dec. 2005 from Erno Keskeny, dated Jan. 4, 2006 (Exhibit 2020, filed in Interference No. 105,893).
Progress Report for Jan. 2006 from Erno Keskeny, dated Jan. 28, 2006 (Exhibit 2021, filed in Interference No. 105,893).
Oxymorphone Process Development Progress Meeting Summary, dated Apr. 19, 2006 (Exhibit 2022, filed in Interference No. 105,893).
Monthly Report for Apr. 2006 from Jen-Sen Dung, dated Apr. 27, 2006 (Exhibit 2023, filed in Interference No. 105,893).
Progress Report for Jul. 2006 from Erno Keskeny, dated Jul. 31, 2006 (Exhibit 2024, filed in Interference No. 105,893).
Aug. 2, 2006 Presentation (Exhibit 2025, filed in Interference No. 105,893).
Report # 2297 of the Chemical Process R&D division, dated Sep. 18, 2006 (Exhibit 2026, filed in Interference No. 105,893).
Specification Committee Meeting Summary, Oct. 9, 2006 (Exhibit 2027, filed in Interference No. 105,893).
Laboratory Notebook # 2053 of Dr. Erno Keskeny, dated Jul. 30, 2004 (Exhibit 2028, filed in Interference No. 105,893).
Laboratory Notebook # 2128 of Dr. Erno Keskeny, dated Jun. 16, 2005 (Exhibit 2029, filed in Interference No. 105,893).
Laboratory Notebook # 2129 of Dr. Erno Keskeny, dated Feb. 13, 2006 (Exhibit 2030, filed in Interference No. 105,893).
Laboratory Notebook # 2193 of Dr. Erno Keskeny, dated Oct. 18, 2006 (Exhibit 2032, filed in Interference No. 105,893).
2033 Laboratory Notebook # 2342 of Dr. Jen-Sen Dung, dated Feb. 4, 2009 (Exhibit 2033, filed in Interference No. 105,893).
Declaration of Dr. Michael Casner, dated Feb. 12, 2013 (Exhibit 2034, filed in Interference No. 105,893).
Declaration of Dr. Robert Marmor, dated Feb. 13, 2013 (Exhibit 2035, filed in Interference No. 105,893).
Declaration of Dr. Ronald Mattson, dated Feb. 12, 2013 (Exhibit 2036, filed in Interference No. 105,893).
Declaration of Dr. Timothy Davies, dated Feb. 7, 2013 (Exhibit 2037, filed in Interference No. 105,893).
Laboratory Notebook #758 of Dr. Timothy Davies, 2003-2004 (Exhibit 2038, filed in Interference No. 105,893).
Declaration of Dr. Nicholas Archer, dated Feb. 7, 2013 (Exhibit 2039, filed in Interference No. 105,893).

(56) References Cited

OTHER PUBLICATIONS

Agenda for Oct. 27, 2005 meeting at Macfarlan Smith (Exhibit 2040, filed in Interference No. 105,893).
Progress Report for Sep. 2005 from Erno Keskeny, dated Sep. 28, 2005 (Exhibit 2041, filed in Interference No. 105,893).
Progress Report for Oct. 2005 from Erno Keskeny, dated Oct. 31, 2005 (Exhibit 2042, filed in Interference No. 105,893).
Monthly Report for Oct. 2005 from Jen-Sen Dung, dated Nov. 1, 2005 (Exhibit 2043, filed in Interference No. 105,893).
Monthly Report for Dec. 2006 from Jen-Sen Dung, dated Jan. 3, 2007 (Exhibit 2044, filed in Interference No. 105,893).
Declaration of Dr. Erno Keskeny, dated Feb. 15, 2013 (Exhibit 2045, filed in Interference No. 105,893).
Corrected version of the Declaration of Dr. Erno Keskeny, admitted during the May 7, 2013 deposition of Dr. Erno Keskeny (Exhibit 2045X, filed in Interference No. 105,893).
Corrected version of the Declaration of Dr. Erno Keskeny, admitted during the May 7, 2013 deposition of Dr. Erno Keskeny (Exhibit 2045Y, filed in Interference No. 105,893).
Monthly Report for Nov. 2007 from Jen-Sen Dung, dated Nov. 29, 2007 (Exhibit 2047, filed in Interference No. 105,893).
Progress Report for Apr. 2006 from Erno Keskeny, dated Apr. 26, 2006 (Exhibit 2048, filed in Interference No. 105,893).
Monthly Report for May 2006 from Jen-Sen Dung, dated May 30, 2006 (Exhibit 2049, filed in Interference No. 105,893).
Progress Report for Jun. 2006 from Erno Keskeny, dated Jun. 26, 2006 (Exhibit 2050, filed in Interference No. 105,893).
Monthly Report for Jun. 2006 from Jen-Sen Dung, dated Jun. 30, 2006 (Exhibit 2051, filed in Interference No. 105,893).
Monthly Report for Jul. 2006 from Jen-Sen Dung, dated Jul. 31, 2006 (Exhibit 2052, filed in Interference No. 105,893).
Progress Report for Aug. 2006 from Erno Keskeny, dated Aug. 24, 2006 (Exhibit 2053, filed in Interference No. 105,893).
Monthly Report for Aug. 2006 from Jen-Sen Dung, dated Aug. 25, 2006 (Exhibit 2054, filed in Interference No. 105,893).
Progress Report for Sep. 2006 from Erno Keskeny, dated Sep. 29, 2006 (Exhibit 2055, filed in Interference No. 105,893).
Progress Report for Oct. 2006 from Erno Keskeny, dated Oct. 29, 2006 (Exhibit 2056, filed in Interference No. 105,893).
Monthly Report for Oct. 2006 from Jen-Sen Dung, dated Nov. 2, 2006 (Exhibit 2057, filed in Interference No. 105,893).
Weiss (1957) "Derivatives of Morphine. II. Demethylation of 14-hydroxycodeinone, 14-hydroxymorphinone and 8,14-Dihydroxydihydromorphinone", *J. Org. Chem.* 22:1505-1508 (Exhibit 2058, filed in Interference No. 105,893).
Coop et al. (1998) "L-Selectride as a General Reagent for the O-Demethylation and N-Decarbomethoxylation of Opium Alkaloids and Derivatives", *J. Org. Chem.* 63:4392-4396 (Exhibit 2059, filed in Interference No. 105,893).
James C. Kraner (2006) *SOFT ToxTalk* 30(3):6 (Exhibit 2060, filed in Interference No. 105,893).
Declaration of James Mencel dated submitted Sep. 17, 2010 in U.S. Appl. No. 11/866,840 (Exhibit 2061, filed in Interference No. 105,893).
Casner et al. U.S Patent No. 7,153,966, issued on Dec. 26, 2006 (Exhibit 2062, filed in Interference No. 105,893).
Chapman et al. U.S. Patent No. 7,129,248, issued on Oct. 31, 2006 (Exhibit 2063, filed in Interference No. 105,893).
Declaration of James Mencel, dated Feb. 18, 2013 (Exhibit 2064, filed in Interference No. 105,893).
Declaration of Erno M. Keskeny, Ph.D., dated Sep. 17, 2010 in U.S. Appl. No. 11/866,840 (Exhibit 2065, filed in Interference No. 105,893).
Declaration of Jen-Sen Dung, Ph.D., dated Feb. 18, 2013 (Exhibit 2066, filed in Interference No. 105,893).
Email from Jen-Sen Dung to Helen Ogden dated Jul. 8, 2005 (Exhibit 2067, filed in Interference No. 105,893).
Email from Suzanne Currie to Jen-Sen Dung dated Jul. 11, 2005 (Exhibit 2068, filed in Interference No. 105,893).
Email from Mel Mitchell to Jen-Sen Dung dated Jul. 20, 2005 (Exhibit 2069, filed in Interference No. 105,893).
Email from Jen-Sen Dung to Mel Mitchell dated Jul. 20, 2005 (Exhibit 2070, filed in Interference No. 105,893).
Email from Mel Mitchell to Jen-Sen Dung dated Jul. 21, 2005 (Exhibit 2071, filed in Interference No. 105,893).
Email from Jen-Sen Dung to Mary Cooke dated Nov. 7, 2005 (Exhibit 2072, filed in Interference No. 105,893).
Email from James Mencel to Jen-Sen Dung, Jennifer Goodall, Robert Hogan, Erno Keskeny dated Apr. 19, 2006, copying Mary Cooke, Ron Rossi and Brian (Exhibit 2073, filed in Interference No. 105,893).
Email from James Mencel to Jen-Sen Dung, Jennifer Goodall, Robert Hogan, Erno Keskeny dated May 1, 2006, copying Ron Rossi and Brian Shaunessy (Exhibit 2075, filed in Interference No. 105,893).
Email from James Mencel to Jen-Sen Dung, Jennifer Goodall, Robert Hogan, Erno Keskeny dated May 11, 2006, copying Brian Fairley (Exhibit 2076, filed in Interference No. 105,893).
Apr. 28, 2004 Draft Process Outline Prepared at Macfarlan Smith for West Deptford (Exhibit 2077, filed in Interference No. 105,893).
Jul. 9, 2004 letter to FDA regarding Jun. 30, 2004 meeting (Exhibit 2078, filed in Interference No. 105,893).
Jun. 6, 2006 Chemical and Analytical Development Key Activities Summary for May 2006 by James Mencel addressed to John Fowler (Exhibit 2079, filed in Interference No. 105,893).
Jul. 10, 2006 Chemical and Analytical Development Key Activities Summary for Jun. 2006 by James Mencel addressed to John Fowler (Exhibit 2080, filed in Interference No. 105,893).
Aug. 4, 2006 Chemical and Analytical Development Key Activities Summary for Jul. 2006 by James Mencel addressed to John Fowler (Exhibit 2081, filed in Interference No. 105,893).
Sep. 8, 2006 Chemical and Analytical Development Key Activities Summary for Aug. 2006 by James Mencel addressed to John Fowler (Exhibit 2082, filed in Interference No. 105,893).
Oct. 9, 2006 Chemical and Analytical Development Key Activities Summary for Oct. [sic, Sep.] 2006 by James Mencel addressed to John Fowler (Exhibit 2083, filed in Interference No. 105,893).
Nov. 6, 2006 Chemical and Analytical Development Key Activities Summary for Oct. 2006 by James Mencel addressed to John Fowler (Exhibit 2084, filed in Interference No. 105,893).
Jan. 9, 2006 Chemical and Analytical Development Key Activities Summary for Dec. 2006 by James Mencel addressed to John Fowler (Exhibit 2086, filed in Interference No. 105,893).
Apr. 27, 2009 Monthly Report for Apr. 2009 from Jen-Sen Dung to James Mencel (Exhibit 2087, filed in Interference No. 105,893).
May 6, 2009 Development Highlights for Apr. 2009 from James Mencel to John Fowler (Exhibit 2088, filed in Interference No. 105,893).
Jan. 29, 2007 Monthly Report for Jan. 2007 from Jen-Sen Dung to James Mencel (Exhibit 2089, filed in Interference No. 105,893).
Feb. 7, 2007 Summary of Key Development Activities for Jan. 2007 from James Mencel to John Fowler (Exhibit 2090, filed in Interference No. 105,893).
HPLC traces corresponding to Exhibit 2012, p. 199, Nov. 26, 2007 (Exhibit 2092, filed in Interference No. 105,893).
HPLC traces corresponding to Exhibit 2012, p. 203, Nov. 28, 2007 (Exhibit 2093, filed in Interference No. 105,893).
HPLC traces corresponding to Exhibit 2012, p. 205, Nov. 28-29, 2007 (Exhibit 2094, filed in Interference No. 105,893).
HPLC traces corresponding to Exhibit 2012, p. 207, Nov. 28-29, 2007 (Exhibit 2095, filed in Interference No. 105,893).
UK Patent Application 0624880.1, filed Dec. 14, 2006 (Exhibit 2096, filed in Interference No. 105,893).
U.S. Patent No. 8,217,175 of Wang et al. (Assignee Mallinckrodt LLC), issued on Jul. 10, 2012 (Exhibit 2097, filed in Interference No. 105,893).
Notice of Allowance, mailed Oct. 21, 2010, in Dung U.S. Appl. No. 11/866,840 (Exhibit 2098, filed in Interference No. 105,893).
HPLC traces corresponding to Exhibit 2011, p. 189, May 11, 2006 (Exhibit 2099, filed in Interference No. 105,893).
Monthly Report for Jan. 2006 from Jen-Sen Dung, dated Feb. 2, 2006 (Exhibit 2100, filed in Interference No. 105,893).

(56) References Cited

OTHER PUBLICATIONS

Declaration of Nisha Patel, dated Feb. 19, 2013 (Exhibit 2101, filed in Interference No. 105,893).
Pages from Johnson Matthey Empower system reflecting Nisha Patel's May-Jun. 2006 confirmation of ABUK content in sample 2128-189 (Exhibit 2103, filed in Interference No. 105,893).
Excerpts from Laboratory Notebooks 844 and 845 of Robert Hogan, Jan. 26, 2006; Apr. 27, 2006 (Exhibit 2104, filed in Interference No. 105,893).
Declaration of Robert Hogan, dated Jul. 12, 2013 (Exhibit 2105, filed in Interference No. 105,893).
Deposition Transcript of Stephen Husbands, Ph.D., dated Aug. 14, 2013 (Exhibit 2106, filed in Interference No. 105,893).
Deposition Transcript of James Janetka, Ph.D., dated Aug. 14, 2013 (Exhibit 2107, filed in Interference No. 105,893).
*Novozymes A/S* v. *DuPont Nutrition Biosciences APS*, No. 12-1433, 15 (Fed. Cir. Jul. 22, 2013) (Exhibit 2108, filed in Interference No. 105,893).
Petition for Inter Partes Review of U.S. Patent No. 7,851,482, filed on Nov. 18, 2013.
Dung et al., U.S. Patent No. 7,851,482, "Method for Making Analgesics" (filed Oct. 3, 2007; issued Dec. 14, 2010) (Exhibit 1001, filed in IPR2014-00160).
Declaration of Kevin Burgess, Ph.D., dated Nov. 18, 2013 (Exhibit 1002, filed in IPR2014-00160).
Buehler et al., U.S. Patent Appl. Pub. No. 2008/0312442, "Process for Preparing Morphinan-6-One Products with Low Levels of Alpha, Beta-Unsaturated Ketone Compounds" (filed Mar. 2, 2007; published Dec. 18, 2008) (Exhibit 1003, filed in IPR2014-00160).
Buehler et al., U.S. Appl. No. 60/778,258, "Process for Preparing Morphinan-6-One Products with Low Levels of α,β-Unsaturated Ketone Compounds" (filed Mar. 2, 2006) (Exhibit 1004, filed in IPR2014-00160).
Amendment dated Nov. 11, 2011 in U.S. Appl. No. 11/915,606 (Exhibit 1006, filed in IPR2014-00160).
FDA Approved Drug Label "OPANA® (Oxymorphone Hydrochloride) Tablets 5 mg and 10 mg" (Jun. 2006) (Exhibit 1008, filed in IPR2014-00160).
Weigl et al., International Pub. No. WO 2006/084412, "Method for Purifying Noroxymorphone Compounds" (filed Feb. 9, 2006; published Aug. 17, 2006) (Exhibit 1009, filed in IPR2014-00160).
Certified English translation of Weigl et al., International Pub. No. WO 2006/084412, "Method for Purifying Noroxymorphone Compounds" (filed Feb. 9, 2006; published Aug. 17, 2006) (Exhibit 1010, filed in IPR2014-00160).
Weigl et al., U.S. Patent No. 8,227,609, "Process for Purifying Noroxymorphone Compounds" (filed Feb. 9, 2006; issued Jul. 24, 2012) (Exhibit 1011, filed in IPR2014-00160).
Berge et al., "Pharmaceutical Salts" *J. Pharm. Sci.* 66:1-19 (1977) (Exhibit 1012, filed in IPR2014-00160).
Chapman et al., U.S. Patent Appl. Pub. No. 2005/0222188, "Process for Preparing Oxycodone Hydrochloride Having Less Than 25 ppm 14-Hydroxycodeinone" (filed Mar. 30, 2005; published Oct. 6, 2005) (Exhibit 1013, filed in IPR2014-00160).
Huang et al., U.S. Patent No. 5,869,669, "Preparation of 14-Hydroxynormporphinones from Normorphinone Dienol Acylates" (filed Jul. 11, 1997; issued Feb. 9, 1999) (Exhibit 1014, filed in IPR2014-00160).
Casner et al., U.S. Patent Appl. Pub. No. 2006/0111383, "Preparation of Oxycodone" (filed Sep. 23, 2005; published May 25, 2006) (Exhibit 1015, filed in IPR2014-00160).
Documents from Patent Interference No. 105,553, *Casner et al.* v. *Chapman et al.*, Mar. 13, 2008 (Exhibit 1016, filed in IPR2014-00160).
Endo Pharmaceuticals, Citizen Petition dated May 13, 2010 (Exhibit 1017, filed in IPR2014-00160).
Department of Health & Human Services, Re: Docket No. FDA-2010-P-0243, dated Nov. 8, 2010 (Exhibit 1018, filed in IPR2014-00160).
*Curriculum Vitae* of Kevin Burgess, Ph.D., 2013 (Exhibit 1019, filed in IPR2014-00160).
Lewenstein et al., U.S. Patent No. 2,806,033, "Morphine Derivative" (filed Aug. 3, 1955; issued Sep. 10, 1957) (Exhibit 1020, filed in IPR2014-00160).
Huang, U.S. Patent No. 8,134,002, "Process for Preparing Oxymorphone" (filed May 2, 2007; issued Mar. 13, 2012) (Exhibit 1021, filed in IPR2014-00160).
Coop et al., U.S. Patent No. 6,291,675, "Methods of O-Demethylation and N-Deprotection" (filed May 21, 1997; issued Sep. 18, 2001) (Exhibit 1022, filed in IPR2014-00160).
Snuparek et al., International Pub. No. WO 2006/019364, "A Method of Preparation of Oxycodone" (filed Aug. 16, 2005; published Feb. 23, 2006) (Exhibit 1023, filed in IPR2014-00160).
Huang et al., U.S. Patent No. 5,922,876, "Preparation of Oxymorphone from Morphine" (filed Jul. 16, 1998; issued Jul. 13, 1999) (Exhibit 1024, filed in IPR2014-00160).
Weiss, "Derivatives of Morphine. II. Demethylation of 14-hydroxycodeinone. 14-Hydroxymorphinone and 8,14-Dihydroxydihydromorphinone" *J. Org. Chem.* 22:1505-1508 (1957) (Exhibit 1025, filed in IPR2014-00160).
Eder et al., "Molecular Mechanisms of DNA Damage Initiated by α,β-Unsaturated Carbonyl Compounds As Criteria for Genotoxicity and Mutagenicity" *Environ. Health Perspect.* 88: 99-106 (1990) (Exhibit 1026, filed in IPR2014-00160).
Eder et al., "The possible role of α,β-unsaturated carbonyl compounds in mutagenesis and carcinogenesis" *Toxicol. Lett.* 67: 87-103 (1993) (Exhibit 1027, filed in IPR2014-00160).
Department of Health & Human Services, Re: PSA1, dated Mar. 24, 2008 (Exhibit 1028, filed in IPR2014-00160).
Wasmuth et al., "A Review of Oxymorphone Hydrochloride (NUMORPHAN*) Analgesia Employed for General Surgery, Including Clinical Experience with Five Hundred and Twenty-Eight Patients" *Cleveland Clin. Q.* 28:262-269 (1961) (Exhibit 1029, filed in IPR2014-00160).
FDA Approved Drug Label "OPANA® ER (Oxymorphone Hydrochloride) Extended-Release Tablets 5 mg, 10 mg, 20 mg, and 40 mg" (Jul. 2006) (Exhibit 1030, filed in IPR2014-00160).
FORM 10-Q, United States Securities and Exchange Commission, for the quarterly period ended Sep. 30, 2006, Endo Pharmaceuticals Holdings Inc. (Exhibit 1031, filed in IPR2014-00160).
Erno M. Keskeny, Notebook No. 2128, pp. 175 and 189, 2006 (Exhibit 1032, filed in IPR2014-00160).
Hudlicky, "Sodium Hydrosulfite is an Effective Reducing Agent," Reductions in Organic Chemistry $2^{nd}$ Edition, pp. 165-169, 1996.
File History of U.S. Patent No. 7,851,482 through Feb. 2, 2013 (Exhibit 1005 filed in IPR2014-00160).
Documents from Patent Interference No. 105,893, *Dung et al.* v. *Buehler et al*, dated Oct. 4, 2012-Sep. 25, 2013 (Exhibit 1007 filed in IPR2014-00160).

\* cited by examiner

PROCESS FOR PREPARING MORPHINAN-6-ONE PRODUCTS WITH LOW LEVELS OF α,β-UNSATURATED KETONE COMPOUNDS

CROSS REFERENCE TO RELATED APPLICATIONS

This application is a national stage application of PCT/US2007/005256, filed Mar. 2, 2007, which claims the benefit of U.S. Provisional Application No. 60/778,258 filed Mar. 2, 2006.

FIELD OF THE INVENTION

The present invention generally relates to processes for preparing morphinan-6-one products. The processes involve reducing the concentration of α,β-unsaturated ketone compounds from reaction mixtures including morphinan-6-one compounds.

BACKGROUND OF THE INVENTION

The morphinan alkaloids represent a family of structurally-related products of great medicinal importance. Particular morphinan compounds of pharmaceutical relevance include, for example, codeine, hydrocodone, hydromorphone, morphine, nalbuphine, nalmefene, naloxone, naltrexone, oxycodone, and oxymorphone. Generally, these compounds are analgesics, which are used extensively for pain relief in the field of medicine due to their action as opiate receptor agonists. However, nalmefene, naloxone, naltrexone, and naltrexone methyl bromide are opiate receptor antagonists, and are used for reversal of narcotic/respiratory depression due to opiate receptor agonists, as addiction therapies, and to reverse other undesirable side effects of opiate agonist use, such as severe constipation.

Morphinan compounds and analogs thereof typically have a ring structure generally corresponding to Formula (1):

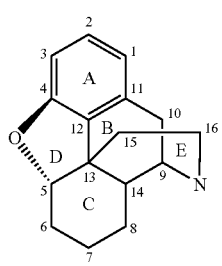

(1)

Various methods are known for the synthesis of morphinan compounds corresponding to Formula (1). Conventional methods used in the commercial production of morphinan compounds typically involve the extraction of opium alkaloids from poppies (*papaver somniferum*). Generally speaking, these processes involve the extraction of the alkaloids from opium in a liquid, precipitation of the alkaloids, separation of the raw alkaloids (e.g., morphine and secondary alkaloids such as papaverine, codeine, and thebaine), and purification of the various alkaloids, optionally followed by semi-synthesis steps to produce particular morphinan compounds. See, for example, Barbier, A., "The Extraction of Opium, Twenty-five years of commercial experience in the treatment of opium," Ann. Pharm. Franc., 1947, 5, 121-40; Barbier, A., "The Extraction of Opium Alkaloids," Bull. Narcotics, 1950, vol. 3, 22-29; Heumann, W, "The Manufacture of Alkaloids from Opium," Bull. Narcotics, 1957, vol. 2, 34-40; Lednicer and Mitscher, Organic Chemistry of Drug Synthesis, chapter 15, (Wiley 1977); French Patent No. 1,000,543 to Penau et al.; British Patent No. 713,689 to Wood et al.; and U.S. Pat. No. 2,009,181 to Kábay.

Synthetic methods for producing various morphinan compounds are also known. These methods commonly utilize 3-methoxy-phenylethylamine as a starting material and include a Grewe cyclization step. For example, in U.S. Pat. No. 4,368,326, Rice discloses a process for preparing a nor-dihydrothebainone (e.g., 1-bromo-N-formylnordihydrothebainone) from a β,γ-hexahydroisoquinolone (e.g., 1-(2'-bromo-4'-methoxy-5'-hydroxybenzyl)-2formyl-1,3,4,5,7,8-hexahydroquinolin-6-one) by Grewe cyclization catalyzed using a super acid catalyst alone or with a combination of an ammonium fluoride complex and trifluoromethanesulfonic acid.

Many pharmaceutically desirable morphinan compounds and analogs thereof have a ketone group on the C-ring of Formula (1) and a saturated bond between the two carbon atoms positioned α and β to the ketone on the C-ring of Formula (1). According to the common nomenclature, the ketone is present on the C(6) carbon atom, with the α and β carbon atoms being the C(7) and C(8) positions (see, e.g., Formula (1)). Thus, these compounds may be referred to as morphinan-6-one compounds. Various processes for producing morphinan-6-one compounds are known, many of which involve some form of catalytic hydrogenation of α,β-unsaturated ketone intermediate compounds at particular points in the process. Commonly used catalysts include, for example, palladium and platinum. For example, in U.S. Pat. No. 6,177,567 to Chiu et al., 14-hydroxycodeinone (an α,β-unsaturated ketone compound) is converted to oxycodone by hydrogenating the α,β-unsaturation using conventional methods such as reduction by diphenylsilane and Pd(Ph₃P)/ZnCl₂, or with sodium hypophosphite in conjunction with a Pd/C catalyst in aqueous acetic acid, or by Pd/C catalytic transfer hydrogenation.

While these and other methods of reducing or removing the α,β-unsaturation are generally effective, α,β-unsaturated ketone compounds may persist as impurities in the final products of desirably α,β-saturated morphinan-6-one products, such as oxycodone. Additionally, known hydrogenation methods may tend to undesirably reduce the ketone as well as reducing or removing the α,β-unsaturation. Further, these and other hydrogenation methods are not normally capable of efficiently and economically reducing the levels of 7,8-unsaturation to below 10 to 100 parts per million, or less.

Some α,β-unsaturated ketone compounds show mutagenic activity in certain tests. Therefore, a need persists for processes for preparing highly pure morphinan-6-one products having a relatively low concentration of α,β-unsaturated ketone compounds present as impurities therein.

SUMMARY OF THE INVENTION

Among the various aspects of the present invention is the provision of a process for the preparation of morphinan-6-one products. The process involves reducing the concentration of α,β-unsaturated ketone compounds which are present as impurities in reaction mixtures including morphinan-6-one compounds. The process generally involves forming a reaction mixture including a morphinan-6-one compound and an α,β-unsaturated ketone compound and treating the reaction mixture with a sulfur-containing compound. In one embodiment, the sulfur-containing compound is a sulfur-containing inorganic acid or salt thereof.

Briefly, therefore, the present invention is directed to a process for the preparation of a morphinan-6-one product, the process comprising:
  forming a reaction mixture comprising a morphinan-6-one compound and an α,β-unsaturated ketone compound;
  treating the reaction mixture with a sulfur-containing compound to reduce the concentration of the α,β-unsaturated ketone compound in the reaction mixture; and
  recovering the morphinan-6-one compound to produce the morphinan-6-one product;
wherein
  the morphinan-6-one compound corresponds to Formula (2):

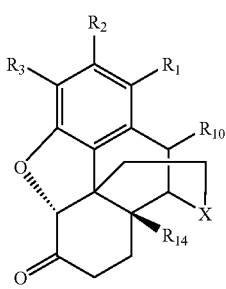

the α,β-unsaturated ketone compound corresponds to Formula (3):

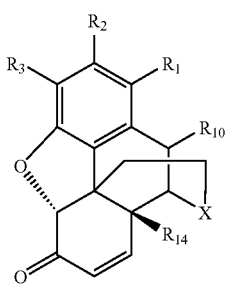

X is —N($R_{17}$)— or —N$^+$($R_{17a}R_{17b}$)—;
$R_1$ and $R_2$ are independently selected from hydrogen, substituted and unsubstituted acyl, acyloxy, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, or nitro;
$R_3$ is hydrogen, hydroxy, protected hydroxy, alkoxy, or acyloxy;
$R_{10}$ is hydrogen, hydroxy, protected hydroxy, halo, keto, tosyl, mesyl, or trifluoromesyl;
$R_{14}$ is hydrogen, hydroxy, or protected hydroxy;
$R_{17}$ is hydrogen, alkyl, cycloalkyl, alkylcarboxy, alkylenecycloalkyl, alkoxycarbonyl, allyl, alkenyl, acyl, aryl, formyl, formyl ester, formamide, benzyl, or an amino protecting group; and
$R_{17a}$ and $R_{17b}$ are independently selected from hydrogen, alkyl, alkenyl, allyl, cycloalkyl, aryl, or benzylyl, and the morphinan-6-one compound comprises less than about 0.1% (by weight) morphinan-6-one product of the α,β-unsaturated ketone compound.

The present invention is also directed to a process for preparing a morphinan-6-one product, the process comprising:
  forming a reaction mixture comprising an α,β-unsaturated ketone compound;
  treating the reaction mixture with a sulfur-containing compound to reduce the α,β-unsaturated ketone compound to form a morphinan-6-one compound; and
  recovering the morphinan-6-one compound to form the morphinan-6-one product,
wherein
  the morphinan-6-one compound corresponds to Formula (2):

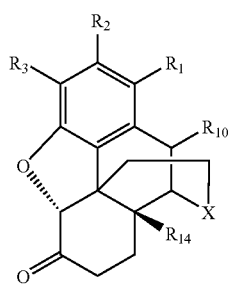

the α,β-unsaturated ketone compound corresponds to Formula (3):

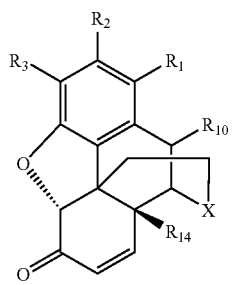

X is —N($R_{17}$)— or —N$^+$($R_{17a}R_{17b}$)—;
$R_1$ and $R_2$ are independently selected from hydrogen, substituted and unsubstituted acyl, acyloxy, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, or nitro;
$R_3$ is hydrogen, hydroxy, protected hydroxy, alkoxy, or acyloxy;
$R_{10}$ is hydrogen, hydroxy, protected hydroxy, halo, keto, tosyl, mesyl, or trifluoromesyl;
$R_{14}$ is hydrogen, hydroxy, or protected hydroxy;
$R_{17}$ is hydrogen, alkyl, cycloalkyl, alkylcarboxy, alkylenecycloalkyl, alkoxycarbonyl, allyl, alkenyl, acyl, aryl, formyl, formyl ester, formamide, benzyl, or an amino protecting group; and
$R_{17a}$ and $R_{17b}$ are independently selected from hydrogen, alkyl, alkenyl, allyl, cycloalkyl, aryl, or benzylyl.

Other objects and features will be in part apparent and in part pointed out hereinafter.

DETAILED DESCRIPTION OF THE INVENTION

The present invention is generally directed to processes for preparing highly pure morphinan-6-one products. The processes generally involve treating a reaction mixture including a morphinan-6-one compound and an α,β-unsaturated ketone compound with a sulfur-containing compound. Advantageously, the process effectively reduces the concentration of undesirable α,β-unsaturated ketone compounds to acceptable levels without removing or otherwise affecting other more desirable compounds or substituent groups or unsaturation thereon. Moreover, the sulfur-containing compound may be utilized to reduce the concentration of α,β-unsaturated ketone compounds present in the reaction mixture from levels of about 0.5% (by weight) or more to levels of not more than about 0.1% (by weight), or lower (e.g., about 0.01% (by weight), about 0.001% (by weight), or lower), with minimal side reactions, ketone reduction, and/or any other undesirable effects.

Morphinan Products and Processes for Preparing the Same

Generally speaking, the morphinan-6-one products of interest in the process of the present invention include morphinan compounds having a keto group at the C(6) carbon atom on the C-ring and a saturated bond between the C(7) and C(8) carbon atoms on the C-ring (i.e., morphinan-6-one compounds). More specifically, the morphinan-6-one compounds are opiate receptor agonists or antagonists generally corresponding to Formula (2):

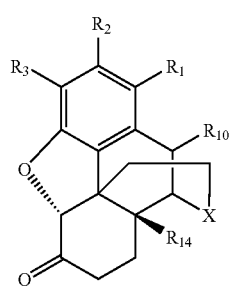

(2)

wherein

X is $-N(R_{17})-$ or $-N^+(R_{71a}R_{17b})-$;

$R_1$ and $R_2$ are independently selected from hydrogen, substituted and unsubstituted acyl, acyloxy, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxyl, or nitro;

$R_3$ is hydrogen, hydroxy, protected hydroxy, alkoxy, or acyloxy;

$R_{10}$ is hydrogen, hydroxy, protected hydroxy, halo, keto, tosyl, mesyl, or trifluoromesyl;

$R_{14}$ is hydrogen, hydroxy, or protected hydroxy;

$R_{17}$ is hydrogen, alkyl, cycroalkyl, alkylcarboxy, alkylenecycloalkyl, alkoxycarbonyl, allyl, alkenyl, acyl, aryl, formyl, formyl ester, formamide, benzyl, or an amino protecting group; and $R_{17a}$ and $R_{17b}$ are independently selected from hydrogen, alkyl, alkenyl, allyl, cycloalkyl, aryl, or benzyl.

When $R_{17}$ is hydrogen, alkyl, alkenyl, cycloalkyl, aryl, or benzyl, salts of the secondary or tertiary amine can be formed wherein the anion is chloride, bromide, acetate, formate, sulfate, bisulfate, bisulfite, oxalate, citrate, malate, tartrate, triflate, trifluoroacetate, methane sulfonate, and the like. When X is $-N^+(R_{17a}R_{17b})-$, the counter-ion can be chloride, bromide, iodide, trifluoroacetate, trifluoromethanesulfonate, methane sulfonate, acetate, p-toluenesulfonate, sulfate, bisulfate, bisulfite, phosphate, hydrogen phosphate, dihydrogen phosphate, fumarate, oxalate, formate, tartrate, benzoate, and the like.

In one preferred embodiment, $R_{14}$ is hydroxy or protected hydroxy. In another preferred embodiment, $R_{14}$ is hydrogen.

In either of the embodiments described above (i.e., when $R_{14}$ is hydroxy or protected hydroxy or $R_{14}$ is hydrogen), $R_3$ is either alkoxy, hydroxy, or protected hydroxy. In one particular embodiment, $R_3$ is methoxy.

In any one of the embodiments described above, X is $-N(R_{17})-$ or $-N^+(R_{17a}R_{17b})-$, wherein $R_{17}$, $R_{17a}$, and $R_{17b}$ are defined as above. Where X is $-N(R_{17})-$, in one particularly preferred embodiment $R_{17}$ is hydrogen, alkyl, alkenyl, alkylcarboxy, or cycloalkyl. Where X is $-N^+(R_{17a}R_{17b})-$, in one particularly preferred embodiment $R_{17a}$ and $R_{17b}$ are independently hydrogen, alkyl, alkenyl, or cycloalkyl.

Representative morphinan-6-one compounds corresponding to Formula (2)(and the various preferred substituent group definitions described above) which can be treated according to the process described herein include, for example, oxymorphone, naloxone, naltrexone, naltrexone methylbromide, nalbuphone, noroxymorphone, hydromorphone, hydrocodone, oxycodone, diethoxycarbonyl-noroxymorphone, salts thereof, and the like. Additionally, derivatives of the above morphinan-6-one compounds which can be treated according to the process described herein include, for example, N-demethylated-, 10-hydroxy-, 10-halo, and 10-keto-morphinan-6-one derivatives, their protected analogs, and the like.

The method of producing the above-described morphinan-6-one compounds for use in the present invention is not narrowly critical, and various methods for producing morphinan-6-one compounds are well known in the art. For example, commercial processing methods for producing morphinan compounds typically involve the extraction of an opium alkaloid (e.g., thebaine) from poppies, followed by various conventional precipitation and purification steps known to those of skill in the art. By way of further example, the morphinan-6-one compound oxycodone may be produced from thebaine in a substantially two-step process, as illustrated in Reaction Scheme 1:

Reaction Scheme 1

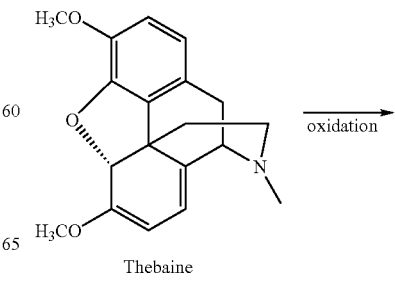

Thebaine

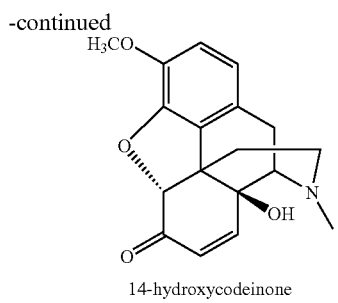

14-hydroxycodeinone

↓ catalytic hydrogenation

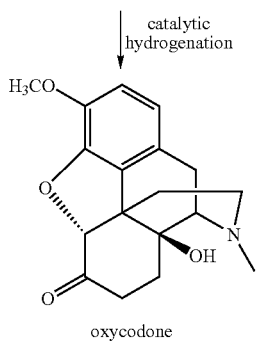

oxycodone

Alternatively, various synthetic methods for producing the above-described morphinan-6-one compounds are also known. In these synthetic methods, a Grewe cyclization reaction is commonly used to form nordihydrothebainone products such as by the processes described in U.S. Pat. Nos. 4,368,326, 4,410,700, 4,521,601, 4,556,712, 4,613,668, 4,727,146, the entire disclosures of which are hereby incorporated by reference herein. Additionally, various methods useful for the semi-synthesis of morphinan compounds and intermediates are known. For example, U.S. Pat. No. 6,177,567 to Chiu et al. and U.S. Pat. No. 6,008,355 to Huang et al. (each of which is hereby incorporated by reference herein) describe methods for the synthesis of oxycodone from codeine. These and other conventional practices are generally applicable in carrying out the preparation of morphinan-6-one compounds and α,β-unsaturated ketone compounds that may be treated according to the processes described herein.

As noted above, in the various conventional processes for producing morphinan-6-one compounds described above, the resulting morphinan product typically also includes some amount of an α,β-unsaturated ketone compound present as an impurity in addition to the desired morphinan-6-one compound. The α,β-unsaturated ketone compounds present as impurities generally correspond to Formula (3):

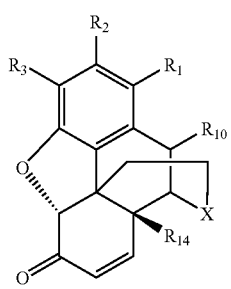

(3)

wherein X, $R_1$, $R_2$, $R_3$, $R_{10}$, and $R_{14}$ are defined as above.

Reaction Conditions

As noted above, the morphinan products produced from conventional processes for preparing morphinan-6-one compounds also yield some amount of an α,β-unsaturated ketone present as an impurity; that is, both the morphinan-6-one compound corresponding to Formula (2) and the α,β-unsaturated ketone compound corresponding to Formula (3) are present in the morphinan product.

The morphinan products produced from conventional morphinan processing methods typically comprise less than about 2% by weight of an α,β-unsaturated ketone compound. Preferably, the morphinan products comprise less than about 1% by weight of an α,β-unsaturated ketone compound. More preferably, the morphinan products comprise less than about 0.8% by weight of an α,β-unsaturated ketone compound. Still more preferably, the morphinan products comprise less than about 0.5% by weight of an α,β-unsaturated ketone compound. As noted above, however, it is desirable to minimize or further minimize the concentration of α,β-unsaturated ketone compounds present in such products.

According to the present invention, a reaction mixture is formed including a morphinan-6-one compound of Formula (2) and an α,β-unsaturated ketone compound of Formula (3). The morphinan-6-one compound and the α,β-unsaturated ketone compound may be produced by any conventional method (such as those described above), and the morphinan-6-one compound may exist as the free base or as a salt, such as the hydrochloride salt. The reaction mixture is treated with a sulfur-containing compound to reduce the concentration of the α,β-unsaturated ketone compound (either by forming additional morphinan-6-one compound or by facilitating the removal of the α,β-unsaturated ketone compound), and the morphinan-6-one compound is recovered to produce the desired morphinan-6-one product. This process is generically illustrated in Reaction Scheme 2, wherein the reaction mixture including the morphinan-6-one compound and the α,β-unsaturated ketone compound is shown in brackets, and X, $R_1$, $R_2$, $R_3$, $R_{10}$, and $R_{14}$ are defined as above.

Reaction Scheme 2

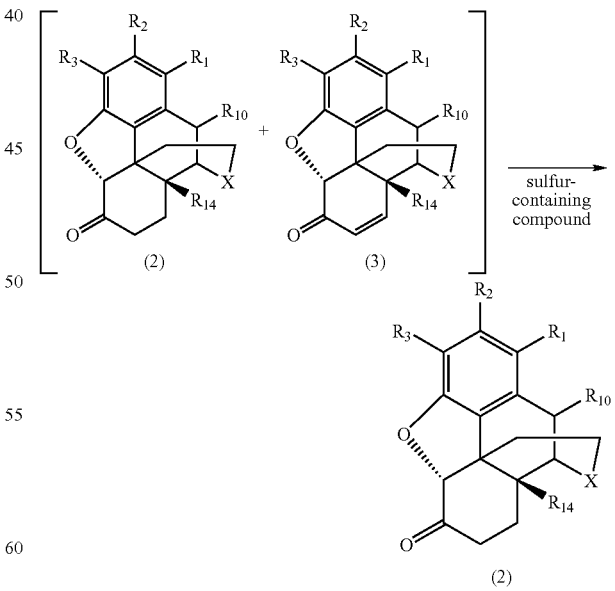

Various reaction mixtures (bracketed) including a morphinan-6-one compound and an α,β-unsaturated ketone compound may be treated according to the processes described herein to yield various highly pure morphinan-6-one products, as illustrated in Reaction Schemes 3-10.

Reaction Scheme 3
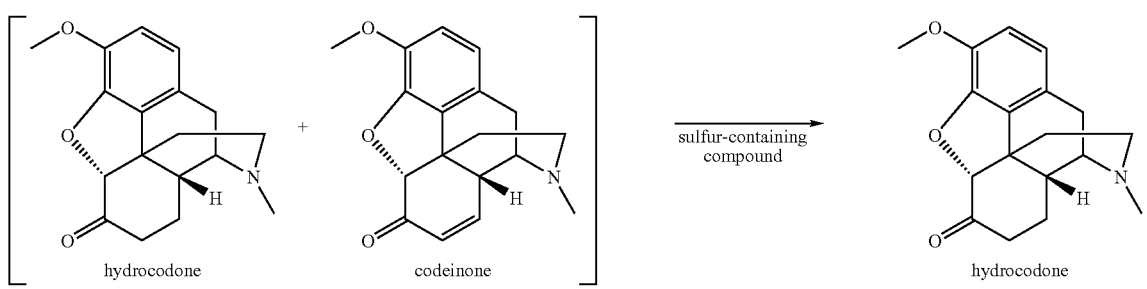
Reaction Scheme 4
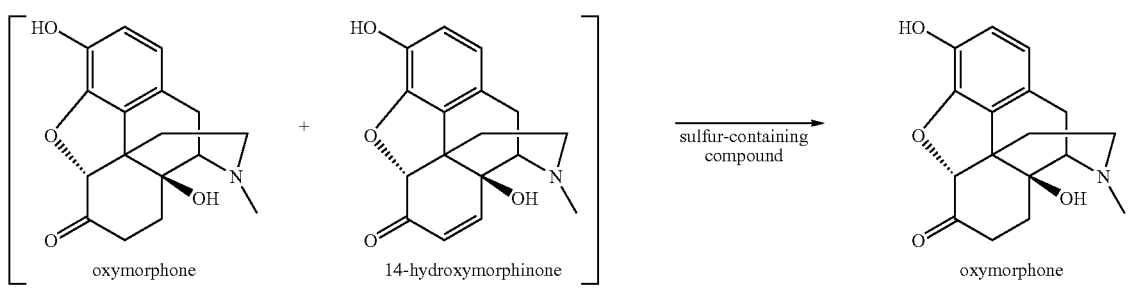
Reaction Scheme 5
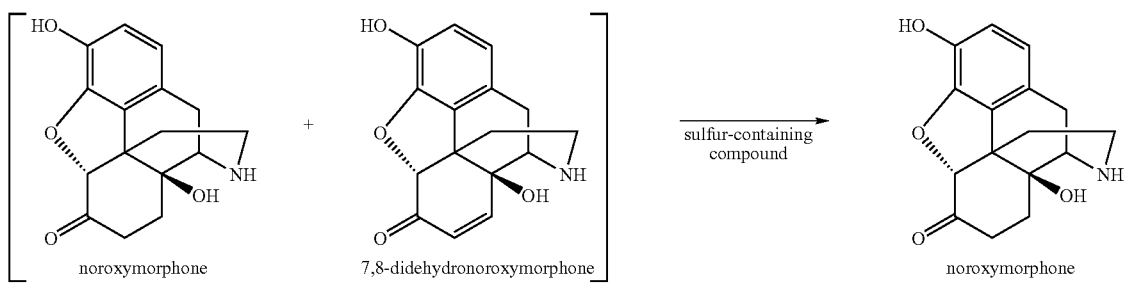
Reaction Scheme 6
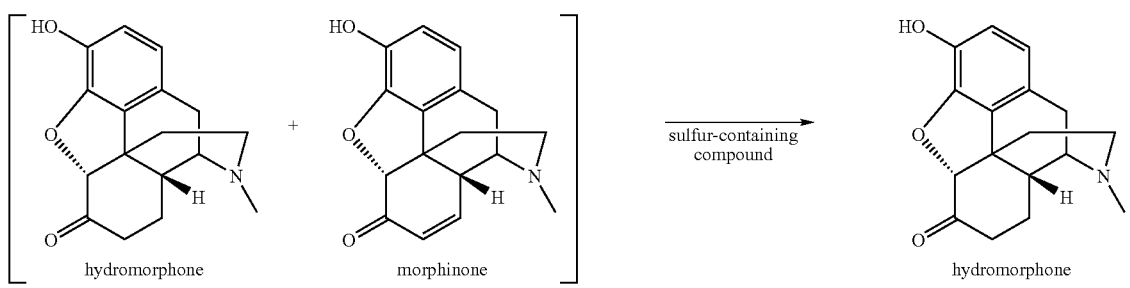

Reaction Scheme 7
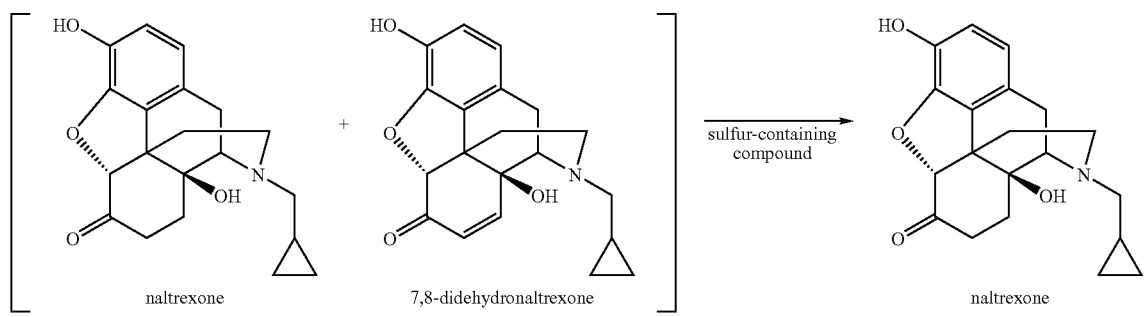
Reaction Scheme 8
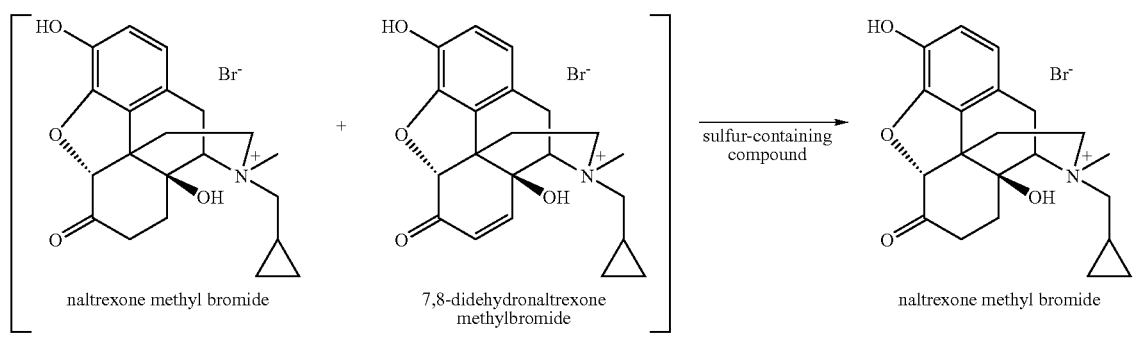
Reaction Scheme 9
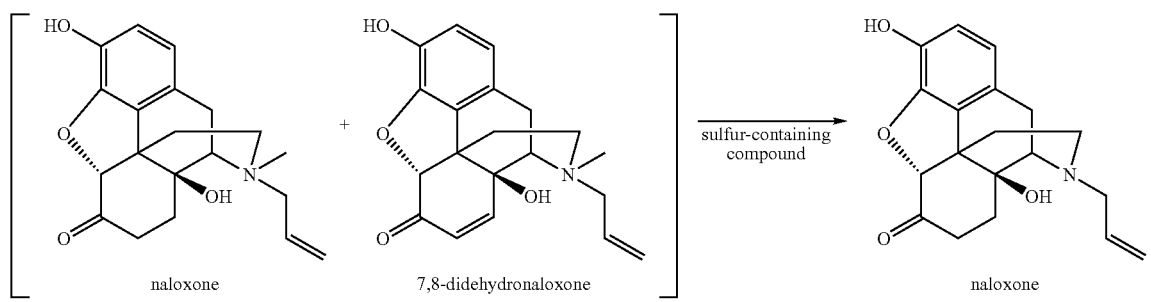
Reaction Scheme 10
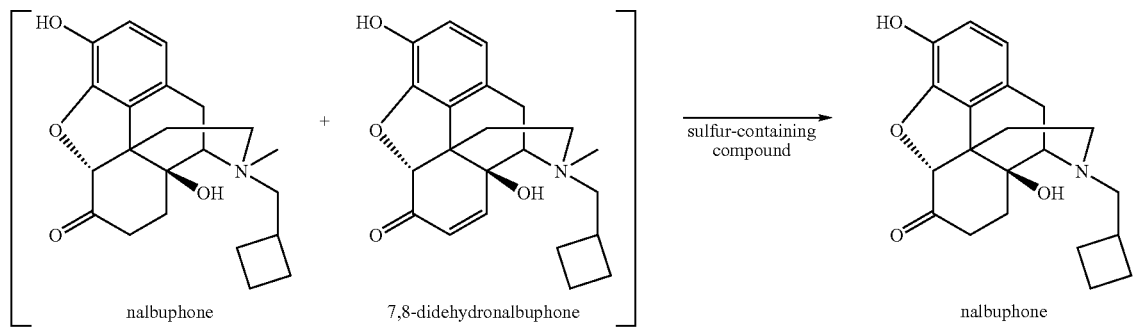

According to various embodiments, the reaction mixture is formed by dissolving or otherwise dispersing the morphinan-6-one compound and the α,β-unsaturated ketone compound in a media material (i.e., a morphinan product including the morphinan-6-one compound and the α,β-unsaturated ketone compound is dispersed in the media material). The reaction mixture is then treated with a sulfur-containing compound. Ideally, the morphinan-6-one compound and the α,β-unsaturated ketone compound are in solution, but a heterogeneous mixture may also be treated according to the processes described herein.

The media material is desirably an aqueous media or an aqueous/organic solvent biphasic media. Exemplary aqueous media for use in the process of the present invention includes, for example, water, water/alcohol mixtures, dilute inorganic solvents such as dilute sulfuric acid, ethereal solvents such as dioxane or tetrahydrofuran, combinations thereof, and the like. Exemplary organic solvents for use in aqueous/organic solvent biphasic media includes, for example, butanone, ethyl acetate, butanol, diethyl ether, benzene, chloroform, tetrachloroethylene, toluene, 1,1,1-trichloroethane, carbon tetrachloride, dibutyl ether, cyclohexane, hexane, dipentyl ether, heptane, hexadecane, combinations thereof, and the like.

Generally, a sufficient amount of media material to substantially solubilize the morphinan-6-one compound and the α,β-unsaturated ketone compound in the reaction mixture is desired. Higher amounts of media material may increase the costs of manufacturing, as the more dilute reaction mixture may require additional process cycle time, or require the removal or excess media material during subsequent processing steps.

The weight ratio of media material to morphinan-6-one compound in the reaction mixture is preferably from about 1:1 to about 50:1. More preferably, the weight ratio of media material to morphinan-6-one compound in the reaction mixture is from about 1:1 to about 25:1. For example, the weight ratio of media material to morphinan-6-one compound in the reaction mixture may be from about 1:1 to about 5:1, from about 1:1 to about 10:1, from about 1:1 to about 15:1, or from about 1:1 to about 20:1. Still more preferably, the weight ratio of media material to morphinan-6-one compound in the reaction mixture is from about 5:1 to about 25:1. For example, the weight ratio of media material to morphinan-6-one compound in the reaction mixture may be from about 5:1 to about 10:1, from about 5:1 to about 15:1, or from about 5:1 to about 20:1. Still more preferably, the weight ratio of media material to morphinan-6-one compound in the reaction mixture is from about 5:1 to about 15:1. For example, the weight ratio of media material to morphinan-6-one compound in the reaction mixture may be from about 5:1 to about 6:1, from about 5:1 to about 7:1, from about 5:1 to about 8:1, from about 5:1 to about 9:1, from about 5:1 to about 10:1, from about 5:1 to about 11:1, from about 5:1 to about 12:1, from about 5:1 to about 13:1, or from about 5:1 to about 14:1. Most preferably, the weight ratio of media material to morphinan-6-one compound in the reaction mixture is from about 5:1 to about 11:1. It will be understood that some portion of the media material may be derived from the sulfur-containing compound itself (e.g., as water of hydration).

Optionally, a phase transfer catalyst may also be added to the aqueous/organic solvent biphasic media. The phase transfer catalyst is preferably any suitable composition for use in the transfer of reactants (i.e., morphinan-6-one compounds, α,β-unsaturated ketone compounds, and/or sulfur-containing compounds) between the aqueous and organic solvent interface. Typically, the phase transfer catalyst is an ammonium-based compound, such as a quaternary ammonium salt. Suitable quaternary ammonium salts for use as phase transfer catalysts include tetraalkylammonium salts such as, for example, tetramethyl-, tetraethyl-, tetrabutyl-, tetrahexyl-, tetraoctyl-, methyltriphenyl-, methyltrioctyl-, benzyltrimethyl-, benzyltriethyl-, benzyltributyl-, hexadecyltrimethyl-ammonium salts, and the like. Suitable salts include, for example, halide, hydroxide, bicarbonate, bisulfate, thiocyanate, tetrafluoroborate, and the like. Other phase transfer catalysts such as phosphonium salts may be suitable as well.

A variety of sulfur-containing compounds may be utilized to treat the reaction mixture and reduce the concentration of the α,β-unsaturated ketone compound according to the processes described herein. In various embodiments, the sulfur-containing compound is a sulfur-containing nucleophile. As utilized herein, "nucleophile" refers to an ion or molecule that donates a pair of electrons to an atomic nucleus to form a covalent bond. In other embodiments, the sulfur-containing compound is a sulfur-containing reducing agent. As utilized herein, "reducing agent" refers to an agent having the ability to add one or more electrons to an atom, ion or molecule. In either of the two embodiments described above (i.e., when the sulfur-containing compound is a sulfur-containing nucleophile or a sulfur-containing reducing agent), the sulfur-containing compound is a compound having the ability to effect the reduction of and/or a 1,4 addition across the α,β-unsaturated bond of the α,β-unsaturated ketone compound.

In one embodiment, the sulfur-containing compound is a sulfur-containing inorganic acid or salt thereof. Suitable sulfur-containing inorganic acids include, for example, hydrosulfuric acid ($H_2S$); sulfurous acid ($H_2SO_3$); persulfuric acid ($H_2SO_5$); thiosulfurous acid ($H_2S_2O_2$); dithionous acid ($H_2S_2O_4$); disulfurous acid ($H_2S_2O_5$); dithionic acid ($H_2S_2O_6$); pyrosulfuric acid ($H_2S_2O_7$); peroxydisulfuric acid ($H_2S_2O_8$); trithionic acid ($H_2S_3O_6$); tetrathionic acid ($H_2S_4O_6$); pentathionic acid ($H_2S_5O_6$); chlorosulfonic acid ($HSO_3Cl$); furosulfonic acid ($HSO_3F$); sulfamic acid ($HSO_3NH_2$); salts thereof; and the like.

Generally, the sulfur-containing inorganic acid salt may be an alkali metal salt or an alkaline earth metal salt. For example, the salt may be a monovalent or divalent cation selected from $Li^+$, $Na^+$, $K^+$, $Rb^+$, $Cs^+$, $Fr^+$, $Be^{2+}$, $Mg^{2+}$, $Ca^{2+}$, $Sr^{2+}$, $Ba^{2+}$, or $Ra^{2+}$. Preferably, the salt is selected from the group consisting of $Li^+$, $Na^+$, $K^+$, $Mg^{2+}$, $Ca^{2+}$, and combinations thereof.

Alternatively, the sulfur-containing inorganic acid salt may be an ammonium salt ($NH_4^+$) or a quaternary ammonium salt. For example, the sulfur-containing inorganic acid salt may be a tetraalkylated ammonium salt; that is, a quaternary ammonium salt substituted with four alkyl groups preferably having from 1 to about 18 carbon atoms. Suitable tetraalkylated ammonium salts include, for example, tetramethylammonium salts, tetraethylammonium salts, tetrapropylammonium salts, tetrabutylammonium salts, and the like.

In one particular embodiment, the sulfur-containing inorganic acid is dithionous acid ($H_2S_2O_4$) or salts thereof. By way of example, salts of dithionous acid include $MHS_2O_4$ and $M_2S_2O_4$, wherein M is selected from alkali metal salts, alkaline earth metal salts, ammonium salt ($NH_4^+$), and quaternary ammonium salts. According to this embodiment, the α,β-unsaturated ketone compound is chemically reduced to form the morphinan-6-one compound upon treatment with the sulfur-containing compound, discussed in further detail below.

In another particular embodiment, the sulfur-containing inorganic acid is selected from the group consisting of sulfurous acid ($H_2SO_3$); disulfurous acid ($H_2S_2O_5$); and salts thereof. By way of example, salts of sulfurous acid and disulfurous acid include $MHSO_3$, $M_2SO_3$, $MHS_2O_5$, and $M_2S_2O_5$ wherein M is selected from alkali metal salts, alkaline earth metal salts, ammonium salt ($NH_4^+$), and quaternary ammonium salts. According to this embodiment, the sulfur-containing inorganic acid or salt thereof is one which dissociates into the bisulfite ion ($HSO_3^-$) and/or the sulfite ion ($SO_3^{2-}$) in the reaction mixture. It will be understood by one of ordinary skill in the art that sulfurous acid ($H_2SO_3$) generally exists as a solution of $SO_2$ (commonly about 6%) in water. The pKa of sulfurous acid ($H_2SO_3$) is about 1.78 and its ionization expression is:

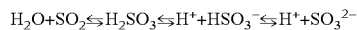

According to this embodiment, various 1,2- and 1,4-sulfonated addition products are formed from the morphinan-6-one compound and the α,β-unsaturated ketone compound by reaction with the bisulfite ion and/or the sulfite ion, discussed in further detail below.

In another particular embodiment, the sulfur-containing compound is a thiol having the formula: R—SH, wherein R is hydrocarbyl, substituted hydrocarbyl, or heterocyclo. For example, R may be substituted or unsubstituted alkyl, alkenyl, alkynyl, or aryl. Exemplary thiols having the formula R—SH, wherein R is defined as above, include alkyl or aryl thiols such as methanethiol, ethanethiol, benzenethiol, and the like. Other exemplary thiols include thiocarboxylic acids and salts thereof (e.g., thiobenzoic acid) and thiol-terminated carboxylic acids and salts thereof (e.g., thioglycolic acid (mercaptoacetic acid), mercaptopropionic acid, and the like). Still other exemplary thiols include amino acids (e.g., L- or D,L-cysteine), other thiol-containing amines and/or quaternary salts thereof (e.g., cysteamine HCl, thiocholine, and the like), or polymer-bound thiols (e.g., polycysteine, polyvinylarylthiol, and the like). In one preferred embodiment, the thiol is benzenethiol. Without being bound to one theory, it is believed that the thiol forms various 1,2- and 1,4-sulfonated addition products from the morphinan-6-one compound and the α,β-unsaturated ketone compound.

The amount of sulfur-containing compound utilized to treat the reaction mixture may vary considerably according to the various reaction mixture components (such as the particular morphinan-6-one compound, the α,β-unsaturated ketone compound, and/or the media material) and concentrations thereof, time of reaction, temperature, pressure, and the like. Relatively high usage rates of sulfur-containing compound generally offer no significant advantages and tend to waste chemicals and/or reactor volume.

The molar ratio of sulfur-containing compound to morphinan-6-one compound in the reaction mixture is typically greater than about 0.5:1. Preferably, the molar ratio of sulfur-containing compound to morphinan-6-one compound in the reaction mixture is from about 0.5:1 to about 3.0:1. For example, the molar ratio of sulfur-containing compound to morphinan-6-one compound in the reaction mixture may be from about 0.5:1 to about 0.8:1, from about 0.5:1 to about 1.0:1, from about 0.5:1 to about 1.5:1, from about 0.5:1 to about 2.0:1, or from about 0.5:1 to about 2.5:1. More preferably, the molar ratio of sulfur-containing compound to morphinan-6-one compound in the reaction mixture is from about 0.6:1 to about 2.8:1. For example, the molar ratio of sulfur-containing compound to morphinan-6-one compound in the reaction mixture may be from about 0.6:1 to about 0.8:1, from about 0.6:1 to about 1.0:1, from about 0.6:1 to about 1.5:1, from about 0.6:1 to about 2.0:1, or from about 0.6:1 to about 2.5:1. Most preferably, the molar ratio of sulfur-containing compound to morphinan-6-one compound in the reaction mixture is from about 0.8:1 to about 2.5:1. For example, the molar ratio of sulfur-containing compound to morphinan-6-one compound in the reaction mixture may be from about 0.8:1 to about 1.0:1, from about 0.8:1 to about 1.2:1, from about 0.8:1 to about 1.4:1, from about 0.8:1 to about 1.6:1, from about 0.8:1 to about 1.8:1, from about 0.8:1 to about 2.0:1, from about 0.8:1 to about 2.2:1, or from about 0.8:1 to about 2.4:1.

The treatment of the reaction mixture with the sulfur-containing compound may be carried out in ambient air or in an oxygen-free environment. Preferably, the treatment is carried out in an inert atmosphere such as, for example, argon or nitrogen gas. The treatment is preferably carried out at a pressure of from about 0.5 atm to about 2.0 atm. More preferably, the treatment is carried out at a pressure of from about 0.75 atm to about 1.5 atm; most preferably from about 0.9 atm to about 1.25 atm.

In various embodiments, the pH of the reaction mixture during treatment with the sulfur-containing compound is greater than about 3. Typically, the pH of the reaction mixture during treatment is less than about 10, although the upper pH limit may depend on the treatment time and/or solubility of the various reaction mixture components. Preferably, the pH of the reaction mixture during treatment with the sulfur-containing compound is from about 3 to about 9; more preferably from about 6 to about 9. For example, the pH of the reaction mixture during treatment with the sulfur-containing compound may be about 3, about 4, about 5, about 6, about 7, about 8, or about 9. Most preferably, the treatment occurs at a pH of from about 6 to about 7.25. Upon the addition of the sulfur-containing compound to the reaction mixture including the morphinan-6-one compound and the α,β-unsaturated ketone compound, the pH may be adjusted to the desired level (e.g. using a base such as ammonium hydroxide). Other suitable bases include, for example, sodium hydroxide, potassium hydroxide, and the like.

The time of reaction is generally a function of the other variables in the reaction, such as pH, ratio of media material to morphinan-6-one compound, amount of sulfur-containing compound, and the like. Typically, some reduction of the concentration of α,β-unsaturated ketone compound in the reaction mixture can be observed after about 1 hour. Preferably, the reaction mixture is treated with the sulfur-containing compound for at least about 1 hour. In some embodiments, the time of reaction is less than about 24 hours. In other embodiments, the time of reaction is from about 1 hour to about 18 hours; in still other embodiments from about 1 hour to about 15 hours; in still other embodiments from about 1 hour to about 10 hours. More preferably, the reaction mixture is treated with the sulfur-containing compound for about 1 hour to about 5 hours. For example, the reaction mixture may be treated with the sulfur-containing compound for about 1 hour, for about 2 hours, for about 3 hours, for about 4 hours, or for about 5 hours.

The temperature of the reaction mixture during treatment with the sulfur-containing compound is generally from about 0° C. to about 100° C. For example, the temperature of the reaction mixture during treatment with the sulfur-containing compound may be from about 10° C. to about 90° C., from about 20° C. to about 80° C., or from about 30° C. to about 70° C. Preferably, the temperature of the reaction mixture during treatment with the sulfur-containing compound is above room temperature. The preferred reaction temperature may vary for each morphinan-6-one. More preferably, the temperature of the reaction mixture during treatment with the sulfur-containing compound is from about 30° C. to about 50° C. For example, the temperature of the reaction mixture during treatment with the sulfur-containing compound may be about 30° C., about 35° C., about 40° C., about 45° C., or about 50° C.

Once the treatment is complete or has proceeded as long as desired, the treated morphinan-6-one compound is recovered to produce the morphinan-6-one product. Advantageously, the morphinan-6-one compound may be recovered from the reaction mixture without the use of an organic solvent. The absence of the need for organic solvents in the recovery process not only provides various environmental and material handling benefits, but also results in a more efficient process suitable for industrial scale applications. Typically, the morphinan-6-one compound is precipitated from the reaction mixture as a base (or salt if desirable) and may then be readily converted into a generally more pharmaceutically acceptable form, if so desired. For example, the pH of the reaction mixture is typically adjusted to about 9-10 or greater with a suitable base such as ammonium hydroxide, and the (desired) precipitated compound recovered. Generally speaking, this pH is at the point wherein opium alkaloids are not ionized. The morphinan-6-one compounds can then be optionally converted into a form more physiologically tolerable, such as the hydrochloride salt, e.g., oxycodone HCl, using conventional methods known to those of skill in the art. For example, the morphinan-6-one base can be dissolved or otherwise dispersed in water, reacted with an acid such as HCl, heated, and cooled to precipitate the morphinan-6-one salt. By way of an alternative example, the morphinan-6-one base can be dissolved or otherwise dispersed in an alcohol solvent (e.g., methanol, ethanol, etc.) or a solvent system (i.e., a mixture of solvents), reacted with concentrated HCl or an HCl/alcohol mixture, and cooled to precipitate the morphinan-6-one hydrochloride salt By way of another example, the morphinan-6-one base can be dissolved or otherwise dispersed in water, alcohol solvent, or a solvent system, reacted with gaseous HCl, heated, and cooled to precipitate the morphinan-6-one hydrochloride salt.

Treatment Reaction Mechanisms

Without being bound to one theory, it is believed that the reduction of the concentration of α,β-unsaturated ketone compounds in the reaction mixture is performed via different mechanisms, depending on the particular sulfur-containing compound selected to treat the reaction mixture.

In one embodiment, the α,β-unsaturated ketone compound is reduced by the sulfur-containing compound to form the desired α,β-saturated morphinan-6-one compound. See, e.g., Camps et al., Tetrahedron Letters, Vol. 29, No. 45, 1988, 5811-5814; Louis-Andre et al., Tetrahedron Letters, Vol. 26, No. 7, 1985, 831-832). By way of example, dithionous acid ($H_2S_2O_4$) and salts thereof (e.g., $MHS_2O_4$ or $M_2S_2O_4$, wherein M is defined as above) operate according to this mechanism; other sulfur-containing compounds, however, may also operate according to the same or a similar mechanism. Reaction Scheme 11 generally illustrates the reduction of the α,β-unsaturated ketone compound (3) to form the desired morphinan-6-one compound (2) according to this embodiment, wherein X, $R_1$, $R_2$, $R_3$, $R_{10}$, and $R_{14}$ are defined as above.

Reaction Scheme 11

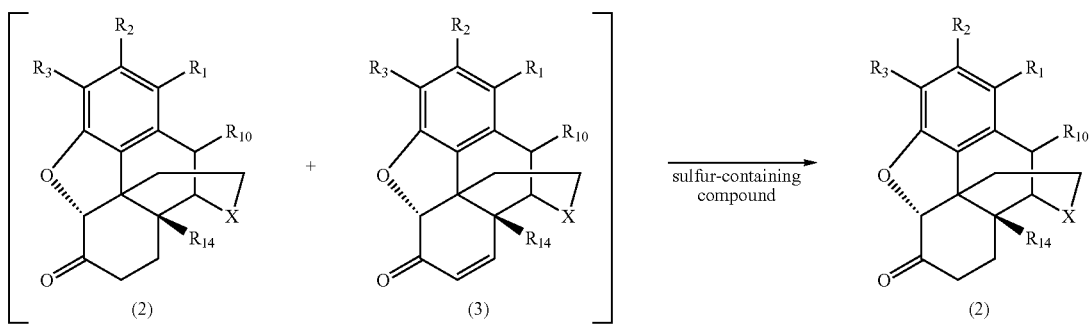

In an alternative embodiment, various 1,2- and 1,4-sulfonated addition products are formed during treatment that assist in the removal of the α,β-unsaturated ketone compounds from the reaction mixture. As noted above, several sulfur-containing compounds dissociate into various sulfur-containing species. In particular, sulfurous acid ($H_2SO_3$), disulfurous acid ($H_2SO_2O_5$), and their salts dissociate into, among other things, bisulfite ($HSO_3^-$) and sulfite ($SO_3^{2-}$).

Bisulfite has been shown to add via radical initiation across isolated double bonds (see, e.g., March, J., Advanced Organic Chemistry, p. 688, J. Wiley & Sons, 1985, 3d. ed.) and/or add via an ionic mechanism (see, e.g., Gilbert, E.; Sulfonation and Related Reactions, p. 152, Interscience, N.Y. 1965; Patai et al., The Chemistry of Alkenes, p. 478, Interscience, London 1965). Without being bound to one theory, it is believed that when the reaction mixture is treated with sulfurous acid, disulfurous acid, or salts thereof and the pH is adjusted to between about 3 and about 9, certain 1,2- and 1,4-addition products and adducts are stably and/or reversibly formed from the α,β-unsaturated ketone compound and the morphinan-6-one compound. It is further believed that the products are generally stable within the pH range of from about 3 to about 9, and adjusting the pH outside of this range after their formation from the α,β-unsaturated ketone compounds and the morphinan-6-one compounds facilitates the removal of the α,β-unsaturated ketone compound from the reaction mixture, resulting in a highly pure morphinan-6-one product.

One preferred embodiment of the present invention is illustrated in Reaction Schemes 12A and 12B, wherein X, $R_1$, $R_2$, $R_3$, $R_{10}$, and $R_{14}$ are defined as above and M is a monovalent or divalent cation. For example, M may be one or more alkali metal or alkaline earth metal monovalent or divalent cations from the sulfur-containing compound. Alternatively, M may be one or more monovalent or divalent cations from the alkaline compound (e.g., NaOH, KOH, $NH_4OH$, etc.) used to adjust the pH of the reaction mixture to between about 3 and about 9 after the addition of the sulfur-containing compound to the reaction mixture.

Reaction Scheme 12A

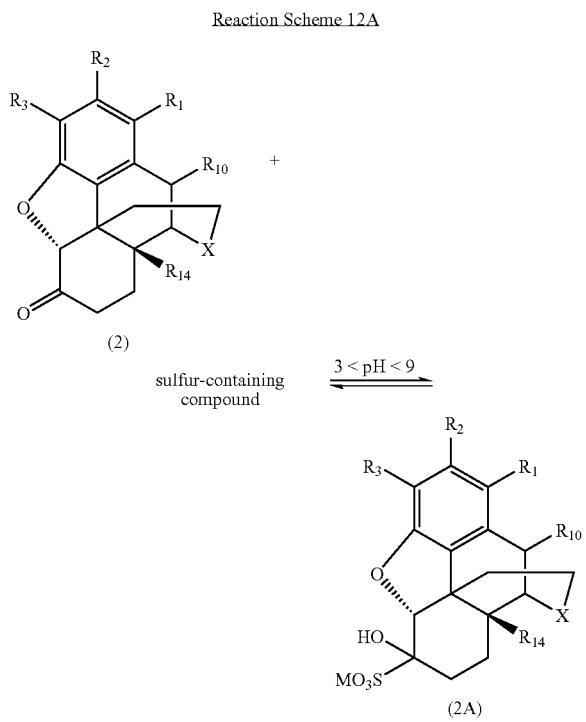

containing compound at a pH of between about 3 and about 9. While it is understood that sulfurous acid, disulfurous acid, and salts thereof operate according to the mechanism illustrated in Reaction Schemes 12A, 12B, and 12C, other sulfur-containing compounds may also operate according to the same or a similar mechanism. For example, thiols (e.g., benzenethiol) may also operate according to the mechanism described in connection with Reaction Schemes 12A, 12B, and 12C.

Particularly, when the reaction mixture is treated with a sulfur-containing compound and the pH of the reaction mixture is adjusted to between about 3 and about 9, the morphinan-6-one compound (2) forms the reversible, water-soluble 1,2-bisulfite adduct (2A). Once the reaction mixture is sufficiently in solution in the media material and/or the sulfur-containing compound, dissociated sulfur specie (such as sulfite and bisulfite) react more readily with the α,β-unsaturated ketone compound (3) also present in the reaction mixture.

As illustrated in Reaction Scheme 12B, one reaction between the α,β-unsaturated ketone compound (3) and the sulfur-containing compound involves the rapid and reversible 1,2-addition of the bisulfite to the carbonyl (similar to the reaction of the sulfur-containing compound with the morphinan-6-one compound illustrated in Reaction Scheme 12A) to form the reversible 1,2-adduct (3A) from the α,β-unsaturated ketone compound (3). Another reaction between the sulfur-containing compound and the α,β-unsaturated ketone com-

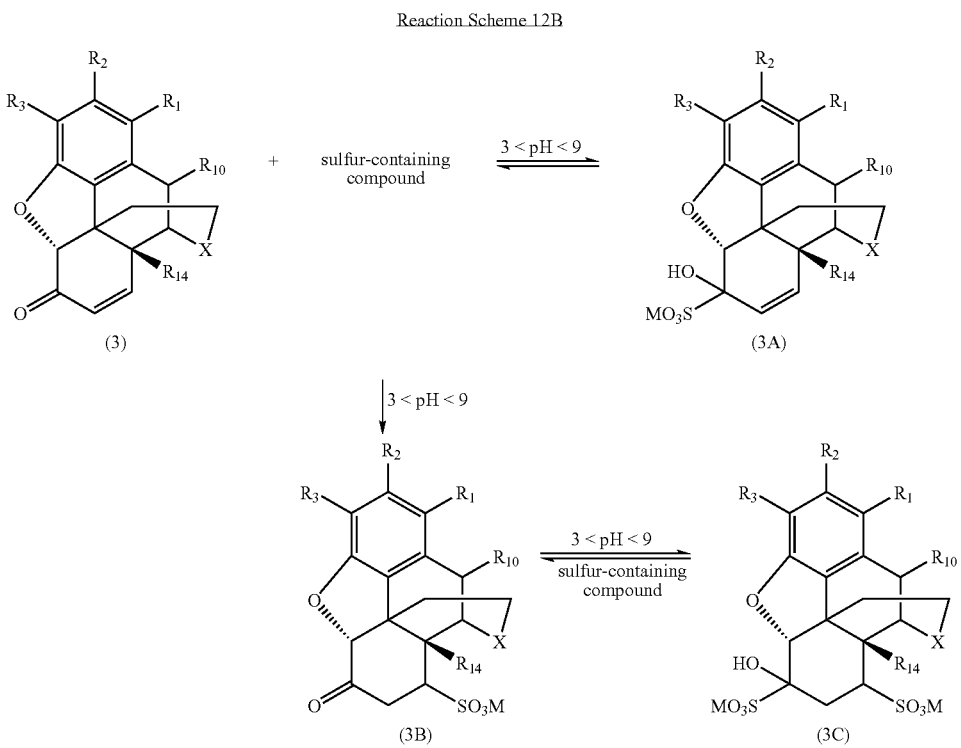

As shown in Reaction Schemes 12A and 12B, various 1,2- and 1,4-sulfonated compounds are formed from the morphinan-6-one compound (2)(scheme 12A) and the α,β-unsaturated ketone compound (3)(scheme 12B) upon treatment of a reaction mixture including these compounds with a sulfur-containing compound at a pH of between about 3 and about 9.

pound (3) is the slower 1,4-addition, forming the more stable 1,4-addition product (3B). The introduction of the sulfonate group in the β-position generally enhances the reactivity of the carbonyl group by destroying its conjugation with the double bond, such that the reversible product is a 1,2- and 1,4-bis adduct (3C)(see Patai et al., *The Chemistry of Alkenes*, p. 478, Interscience, London 1965).

Reaction Scheme 12C illustrates the removal of certain addition products formed in the reaction mixture according to Reaction Schemes 12A and 12B and the resulting highly pure morphinan-6-one product, wherein X, $R_1$, $R_2$, $R_3$, $R_{10}$, $R_{14}$, and M are defined as above.

the pH outside of the range between about 3 and about 9 (i.e., the pH is adjusted to less than about 3 or the pH is adjusted to greater than about 9) with an acid (e.g., sulfuric acid ($H_2SO_4$)) or a base (e.g., ammonium hydroxide ($NH_4OH$)) results in the decomposition of the 1,2-addition products of each compound, rendering the desired morphinan-6-one compound (2) insoluble in water. The relatively more stable 1,4-addition

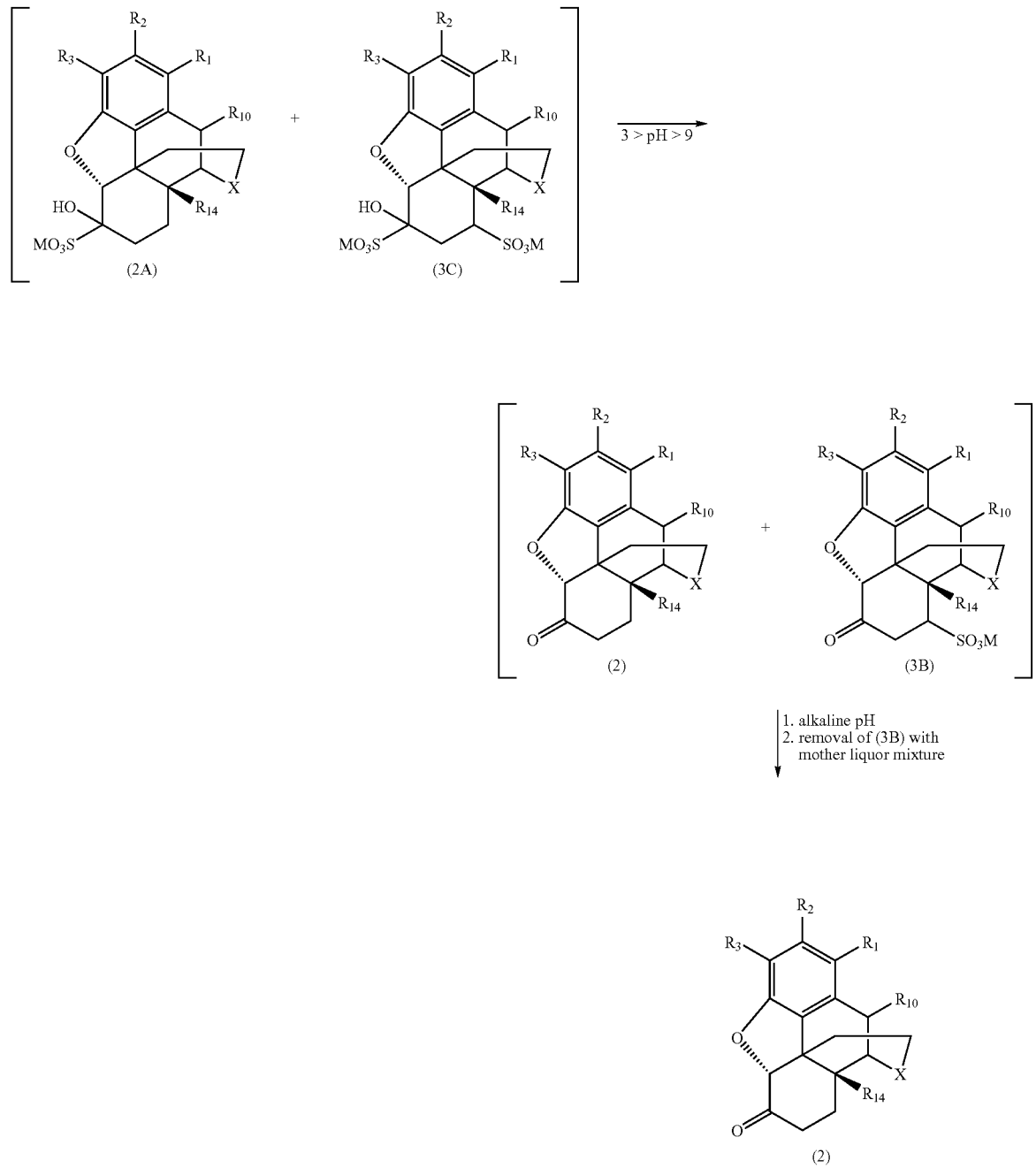

Reaction Scheme 12C

As illustrated in Reaction Scheme 12C, the removal of the α,β-unsaturated ketone addition products is generally based in the differences in solubility of the 1,4-addition product (3B) generated from the α,β-unsaturated ketone compound and the desired morphinan-6-one compound (2). Adjusting product (3B) formed from the α,β-unsaturated ketone compound remains and is water-soluble in the final mixture at an alkaline pH (e.g., pH ~9 or greater). The 1,4-addition product (3B) may thus be removed from the mixture with the mother liquor, leaving the insoluble morphinan-6-one base (2). The desired morphinan-6-one base may then be converted into a more physiologically-tolerable salt form, such as the hydrochloride salt, using methods known to those of skill in the art.

One particularly preferred embodiment of the present invention is illustrated in Reaction Schemes 13A and 13B, wherein M is defined as above.

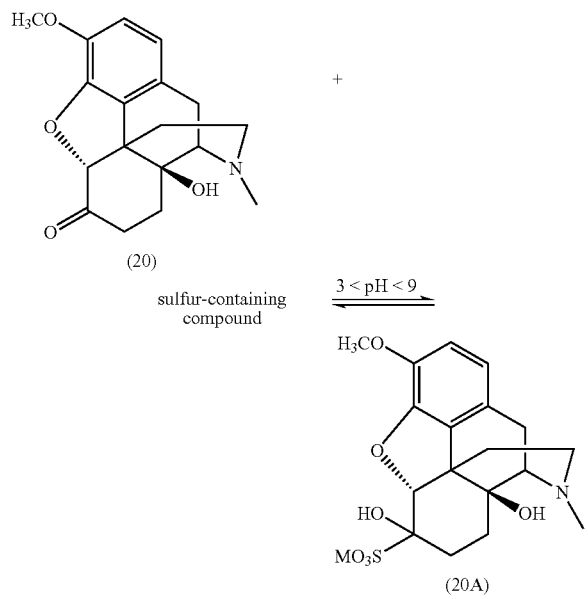

containing compound at a pH of between about 3 and about 9. As discussed above, while it is generally understood that sulfurous acid, disulfurous acid, and salts thereof operate according to the mechanism described in Reaction Schemes 13A and 13B, other sulfur-containing compounds may also operate according to the same or a similar mechanism.

Particularly, when the reaction mixture is treated with a sulfur-containing compound and the pH of the reaction mixture is adjusted to between about 3 and about 9, oxycodone (20) forms the reversible, water-soluble 1,2-bisulfite adduct (20A). Once the reaction mixture is sufficiently in solution in the media material and the sulfur-containing compound, dissociated sulfur specie (such as sulfite and bisulfite) react more readily with the 14-hydroxycodeinone (30) also present in the reaction mixture.

As illustrated in Reaction Scheme 13B, one reaction between 14-hydroxycodeinone (30) and the sulfur-containing compound involves the rapid and reversible 1,2-addition of the sulfite to the carbonyl (similar to the reaction of the sulfur-containing compound with oxycodone illustrated in Reaction Scheme 13A) to form the reversible 1,2-adduct (30A) from 14-hydroxycodeinone. Another reaction between the sulfur-containing compound and 14-hydroxycodeinone (30) is the slower 1,4-addition, forming the more stable 1,4-addition product (30B). The introduction of the sulfonate group in the β-position generally enhances the reactivity of the carbonyl group by destroying its conjugation with the double bond, such that the reversible product is a 1,2- and 1,4-bis adduct (30C)(see Patai et al., *The Chemistry of Alkenes*, p. 478, Interscience, London 1965).

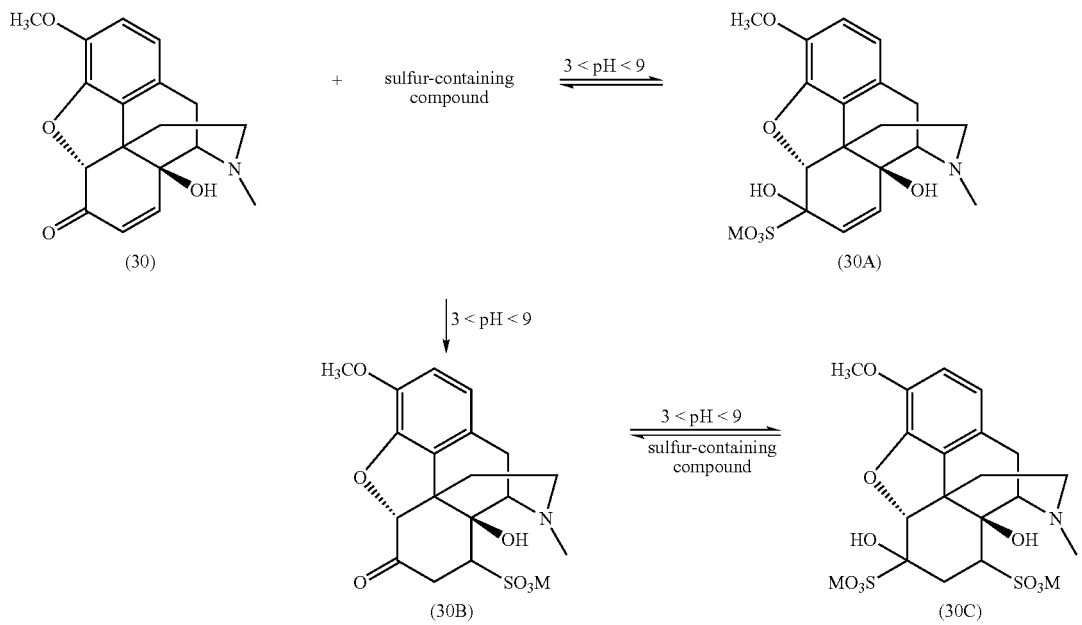

As shown in Reaction Schemes 13A and 13B, various sulfonated compounds are formed from oxycodone (20) (scheme 13A) and the α,β-unsaturated ketone compound 14-hydroxycodeinone (30)(scheme 13B) upon treatment of a reaction mixture including these compounds with a sulfur- Reaction Scheme 13C illustrates the removal of certain addition products formed in the reaction mixture according to Reaction Schemes 13A and 13B and the resulting highly pure oxycodone, wherein M is defined as above.

Reaction Scheme 13C

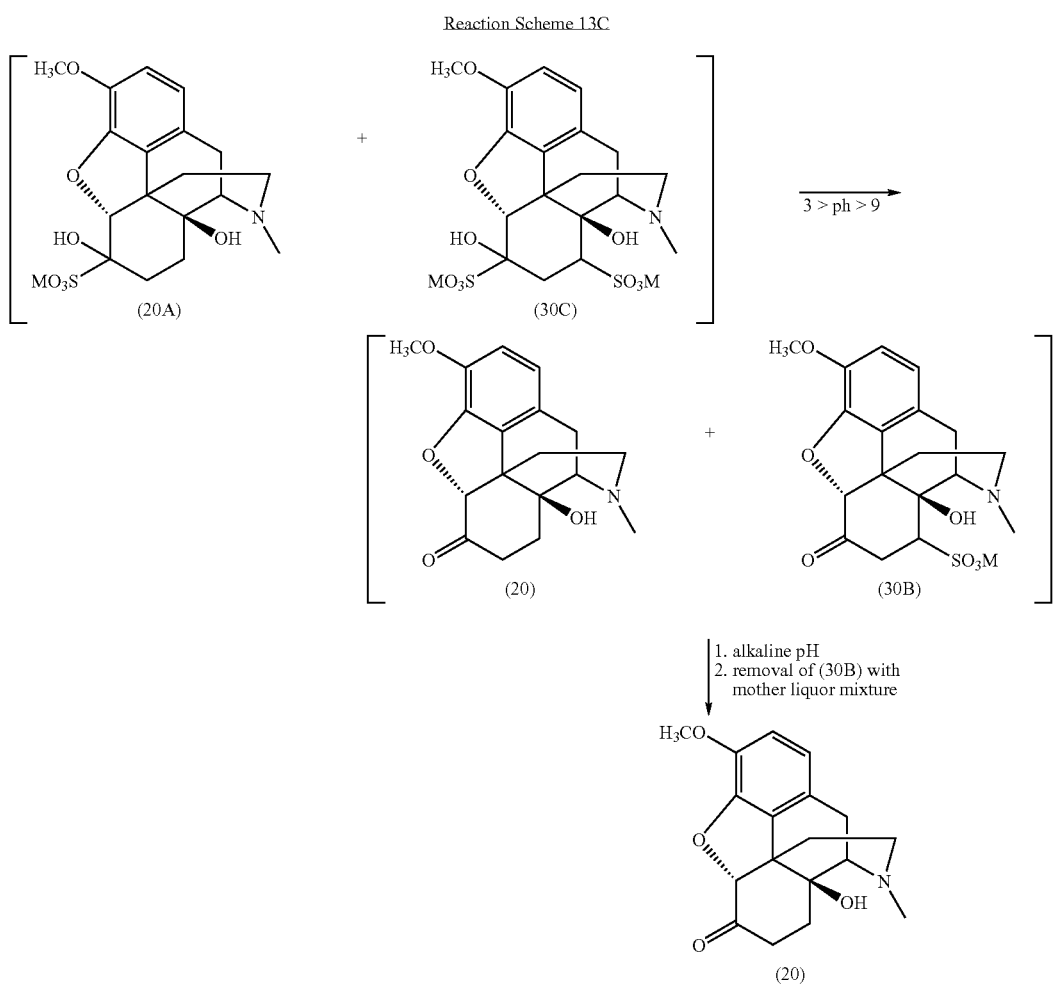

As illustrated in Reaction Scheme 13C, the removal of the 14-hydroxycodeinone addition products is generally based on the differences in solubility of the 1,4-addition product (30B) generated from 14-hydroxycodeinone and the desired oxycodone (20). Adjusting the pH outside of the range between about 3 and about 9 (i.e., the pH is adjusted to less than about 3 or greater than about 9) with an acid (e.g., sulfuric acid ($H_2SO_4$)) or a base (e.g., ammonium hydroxide ($NH_4OH$)) results in the decomposition of the 1,2-addition products of each compound, rendering the desired oxycodone (20) insoluble in water. The relatively more stable 1,4-addition product (30B) formed from 14-hydroxycodeinone remains and is water soluble in the final mixture at an alkaline pH (e.g., pH ~9 or greater). The 1,4-addition product (30B) may thus be removed from the mixture with the mother liquor, leaving the insoluble oxycodone base (20). The oxycodone base may then be converted into a more physiologically-tolerable salt form, such as the hydrochloride salt, using methods known to those of skill in the art.

Removal of Residual Sulfur-Containing Species from the Reaction Mixture

Using the process described herein to reduce the concentration of α,β-unsaturated ketone compounds from a reaction mixture by treating the reaction mixture with a sulfur-containing compound may result in the undesirable accumulation of residual sulfur-containing species (such as sulfites and bisulfites) in the reaction mixture and/or final morphinan-6-one product. Accordingly, the residual sulfur-containing species may be optionally substantially removed from the reaction mixture following the treatment with the sulfur-containing compound using a variety of methods known to those of skill in the art.

As described above, in various embodiments 1,2- and 1,4-sulfonated addition products may be formed by the reaction of a sulfur-containing compound with the morphinan-6-one compound and the α,β-unsaturated ketone compound at a pH of between about 3 to about 9. The adjustment of the pH outside of this range eliminates the 1,2-addition products, renders the morphinan-6-one compound insoluble in water, and the remaining water soluble 1,4-addition product can be removed in the waste stream.

To optionally substantially remove the residual sulfur-containing species upon completion of the reaction with the sulfur-containing compound, the pH of the reaction mixture may be adjusted to less than about 3 (instead of adjusting the pH to greater than 9) with an acid (e.g., sulfuric acid ($H_2SO_4$)) and manipulated prior to the precipitation of the morphinan-6-one compound as described in detail above. More preferably, the pH is adjusted to less than about 2. The reduction in pH converts any residual sulfur species that may be present in the reaction mixture into $SO_2$ gas, which typically has a limited solubility in water. In one embodiment, the $SO_2$ gas may then be optionally heat refluxed out of the reaction mixture by conventional means known to those of skill in the art. Typically, the reaction mixture is heat refluxed for about 2 hours to about 5 hours. The temperature and pressure during reflux are also generally variable. For example, the temperature of the reaction mixture during reflux is typically from about 20° C. to about 100° C., and the reflux may be performed at a pressure of from about 0.003 atm to about 1.0 atm. Alternatively, substantially all of the water (and the $SO_2$ gas) may be optionally distilled off to a receiver tank and discarded. This procedure is also generally known to those of skill in the art.

As discussed above, after treatment of the reaction mixture with the sulfur-containing compound to reduce the concentration of the $\alpha,\beta$-unsaturated ketone compound in the reaction mixture, the morphinan-6-one compound is recovered to produce the desired morphinan-6-one product. Generally speaking, recovery refers to one or more of the precipitation, filtration and drying of the morphinan-6-one base, the formation of the physiologically acceptable morphinan-6-one salt (e.g., the hydrochloride salt), the removal of the residual sulfur-containing species, and/or combinations thereof, to produce a morphinan-6-one product.

The treatment of the reaction mixture with a sulfur-containing compound according to the various processes and embodiments described herein significantly reduces the concentration of $\alpha,\beta$-unsaturated ketone compounds in the reaction mixture, and a highly pure morphinan-6-one product may be produced therefrom. Typically, the morphinan-6-one product comprises less than about 0.1% (by weight morphinan-6-one product) of an $\alpha,\beta$-unsaturated ketone compound. For example, the morphinan-6-one product may comprise less than about 0.05% (by weight morphinan-6-one product) of an $\alpha,\beta$-unsaturated ketone compound Preferably, the morphinan-6-one product comprises less than about 0.01% (by weight morphinan-6-one product) of an $\alpha,\beta$-unsaturated ketone compound. For example, the morphinan-6-one product may comprise less than about 0.005% (by weight morphinan-6-one product) of an $\alpha,\beta$-unsaturated ketone compound. More preferably, the morphinan-6-one product comprises less than about 0.001% (by weight morphinan-6-one product) of an $\alpha,\beta$-unsaturated ketone compound. For example, the morphinan-6-one product may comprise less than about 0.0005% (by weight morphinan-6-one product) of an $\alpha,\beta$-unsaturated ketone compound. Still more preferably, no detectable amount of an $\alpha,\beta$-unsaturated ketone compound is present in the morphinan-6-one product.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, allyl, benzyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen," "halide" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics such as furyl, pyridyl, oxazoiyl, pyrrolyl, indolyl, quinolinyl, or isoquinolinyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, arytoxy, halogen, amido, amino, nitro, cyano, thiol, ketals, acetals, esters and ethers.

The term "acyl," as used herein alone or as part of another group, denotes the moiety formed by removal of the hydroxy group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The term "hydroxy protecting group" refers to hydrocarbyl and substituted hydrocarbyl moieties which bond to an hydroxy oxygen atom in a molecule so as to protect that oxygen atom from further reaction during synthesis. This protection allows reactions to occur selectively at another reaction site on the same molecule. Examples of hydroxy protecting groups include, but are not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro.

Having described the invention in detail, it will be apparent that modifications and variations are possible without departing the scope of the invention defined in the appended claims.

Furthermore, it should be appreciated that all examples in the present disclosure are provided as non-limiting examples.

EXAMPLE 1

In this Example, an oxycodone HCl sample was treated with a sulfur-containing compound according to the processes described herein.

To a 250 ml, 3 neck round bottom flask equipped with a mechanical stirrer, $N_2$ inlet, and thermocouple for temperature control was added 10 g of oxycodone HCl (0.028 moles; >0.3% by weight 14-hydroxycodeinone (14-OHC) impurity). Next, with mixing 100 g of deoxygenated water (10 minute $N_2$ purge) was added. The solution pH was adjusted to about 6 with ammonium hydroxide. Next, 5.0 g of sodium dithionite ($Na_2S_2O_4$) was added. The pH was then adjusted to about 7 with concentrated ammonium hydroxide. The resulting mixture was stirred at 70° C. for about 16 hours.

After about 16 hours, the pH was adjusted to about 9 with ammonium hydroxide, precipitating the oxycodone base. The mixture was stirred for about 1 hour, and the precipitated oxycodone base was filtered, washed with water, and dried overnight at 40° C. under reduced pressure.

The oxycodone base sample was converted to the oxycodone HCl salt by dissolving about 14.5 g of the oxycodone base in a 100 ml, 3 neck round bottom flask equipped with a mechanical stirrer, $N_2$ inlet, and thermocouple for temperature control. Next, with mixing about 29 g of $H_2O$ and about 12.6 g of concentrated HCl was added. The resulting mixture was heated to about 65° C.-75° C. until substantially all was in solution. The heat was then removed, resulting in the precipitation of the oxycodone HCl salt. The precipitated mixture was stirred for about 1-3 hours at less than about 10° C. and filtered to collect the precipitated oxycodone HCl.

The 14-hydroxycodeinone (14-OHC) content was analyzed in the oxycodone base sample and the oxycodone HCl sample using an Agilent HPLC with MS interface capability. The results are illustrated in Table 1.

TABLE 1

| Initial 14-OHC content (% by wt.) | Final 14-OHC content | |
|---|---|---|
| | Oxycodone base (% by wt.) | Oxycodone HCl (% by wt.) |
| 0.3 | 0.0005 | 0.0005 |

EXAMPLES 2A-2G

In Examples 2A-2G, an oxycodone HCl sample was treated with a sulfur-containing compound according to the processes described herein. The treatment was performed at various temperatures, times of reaction, concentration of reactants, and pH.

Example 2A

To a 100 ml, 3 neck round bottom flask equipped with a mechanical stirrer, $N_2$ inlet, and thermocouple for temperature control was added 9.2 g of wet oxycodone HCl (0.02 moles; 0.13% by weight 14-hydroxycodeinone (14-OHC) impurity). Next, with mixing 36.2 g of $H_2O$ and 40.3 g of 6 wt. % $SO_2/H_2O$ solution was added. The resulting mixture was heated to about 30° C. and the solution pH was adjusted to about 6 with ammonium hydroxide. The mixture was stirred for about 3 hours. The pH of the mixture was then adjusted to about 8.8-9.8 with concentrated ammonium hydroxide and stirred for about 30 minutes. The precipitated oxycodone base was then filtered from the mother liquor, washed with about 25.73 g of $H_2O$, and dried. The 14-hydroxycodeinone content (14-OHC) in the oxycodone base was then measured as described in the preceding Example.

The experiment was repeated using identical reagents, amounts thereof, and conditions to form the oxycodone base sample. This oxycodone base sample was converted to the oxycodone HCl salt as described in the preceding example. The 14-hydroxycodeinone content (14-OHC) in the oxycodone base sample and the oxycodone HCl sample were then measured.

Results and reaction conditions for this experiment are illustrated in Table 2.

TABLE 2

| Trial | Temperature (° C.) | Time (hr.) | pH | Concentration (g $H_2O$ per g Oxycodone HCl) | Molar Ratio of $SO_2$ to Oxycodone HCl | Initial 14-OHC content (% by wt.) | Final 14-OHC content | |
|---|---|---|---|---|---|---|---|---|
| | | | | | | | Oxycodone base (% by wt.) | Oxycodone HCl (% by wt.) |
| 1 | 30 | 3 | 6 | 10.2 | 1.8:1 | 0.13 | 0.0007 | Not tested |
| 2 | 30 | 3 | 6 | 10.2 | 1.8:1 | 0.13 | 0.0007 | 0.0007 |

Example 2B

This Example was performed according to the process described in Example 2A. However, in this Example 9.4 g of wet oxycodone HCl (0.02 moles; 0.13% by weight 14-hydroxycodeinone (14-OHC) impurity) was mixed with about 34.6 g of $H_2O$ and about 27.4 g of 6 wt. % $SO_2/H_2O$ solution. The mixture was heated to about 50° C. Next, the pH was adjusted to about 7 using ammonium hydroxide.

The resulting mixture was allowed to react for either 1 hour or 5 hours. At the end of the desired reaction time, the solution was adjusted to a pH of 8.8-9.8 with about 2.0 g of concentrated ammonium hydroxide and stirred for about 30 minutes. The solids were filtered and washed with about 28.0 g of $H_2O$ and dried. The 14-hydroxycodeinone (14-OHC) content in the resulting oxycodone base was measured, as was the 14-hydroxycodeinone (14-OHC) content in the oxycodone HCl salt formed according to the method described in the preceding example. The results and reaction conditions in the various trials are illustrated in Table 3.

TABLE 3

| Trial | Temperature (° C.) | Time (hr.) | pH | Concentration (g $H_2O$ per g Oxycodone HCl) | Molar Ratio of $SO_2$ to Oxycodone HCl | Initial 14-OHC content (% by wt.) | Final 14-OHC content | |
|---|---|---|---|---|---|---|---|---|
| | | | | | | | Oxycodone base (% by wt.) | Oxycodone HCl (% by wt.) |
| 3 | 50 | 1 | 7 | 8.2 | 1.2:1 | 0.13 | None detected | None detected |
| 4 | 50 | 5 | 7 | 8.2 | 1.2:1 | 0.13 | 0.00005 | 0.0005 |

Example 2C

This Example was performed according to the process described in Example 2A. However, in this Example 9.1 g of wet oxycodone HCl (0.02 moles; 0.13-0.14% by weight 14-hydroxycodeinone (14-OHC) impurity) was mixed with about 7.0 g of $H_2O$ and about 52.8 g of 6 wt. % $SO_2/H_2O$ solution. The mixture was heated to either 10° C. or 50° C. Next, the pH was adjusted to 7 using ammonium hydroxide.

The resulting mixture was allowed to react for either 1 hour or 5 hours. At the end of the desired reaction time, the solution was adjusted to a pH of 8.8-9.8 with about 2.0-2.5 g of concentrated ammonium hydroxide and stirred for about 30 minutes. The solids were filtered and washed with about 28.0 g of $H_2O$ and dried. The 14-hydroxycodeinone (14-OHC) content in the resulting oxycodone base was measured, as was the 14-hydroxycodeinone (14-OHC) content in the oxycodone HCl salt formed by the method described in the preceding example. The results and reaction conditions in the various trials are illustrated in Table 4.

TABLE 4

| Trial | Temperature (° C.) | Time (hr.) | pH | Concentration (g $H_2O$ per g Oxycodone HCl) | Molar Ratio of $SO_2$ to Oxycodone HCl | Initial 14-OHC content (% by wt.) | Final 14-OHC content Oxycodone base (% by wt.) | Final 14-OHC content Oxycodone HCl (% by wt.) |
|---|---|---|---|---|---|---|---|---|
| 5 | 50 | 1 | 7 | 8.2 | 2.4:1 | 0.13 | None detected | 0.0006 |
| 6 | 50 | 5 | 7 | 8.2 | 2.4:1 | 0.13 | 0.00015 | 0.0004 |
| 7 | 10 | 5 | 7 | 8.2 | 2.4:1 | 0.14 | 0.001 | Not tested |

Example 2D

This Example was performed according to the process described in Example 2A. However, in this Example 9.52 g of wet oxycodone HCl (0.02 moles; 0.13% by weight 14-hydroxycodeinone (14-OHC) impurity) was mixed with about 72.24 g of $H_2O$ and about 27.76 g of 6 wt. % $SO_2/H_2O$ solution. The mixture was heated to about 50° C. Next, the pH was adjusted to about 7 using ammonium hydroxide.

The resulting mixture was allowed to react for either 1 hour or 5 hours. At the end of the desired reaction time, the solution was adjusted to a pH of 8.8-9.8 with about 2.0-2.5 g of concentrated ammonium hydroxide and stirred for about 30 minutes. The solids were filtered and washed with about 28.0 g of $H_2O$ and dried. The 14-hydroxycodeinone (14-OHC) content in the resulting oxycodone base was measured, as was the 14-hydroxycodeinone (14-OHC) content in the oxycodone HCl salt formed by the method described in the preceding example. The results and reaction conditions in the various trials are illustrated in Table 5.

TABLE 5

| Trial | Temperature (° C.) | Time (hr.) | pH | Concentration (g $H_2O$ per g Oxycodone HCl) | Molar Ratio of $SO_2$ to Oxycodone HCl | Initial 14-OHC content (% by wt.) | Final 14-OHC content Oxycodone base (% by wt.) | Final 14-OHC content Oxycodone HCl (% by wt.) |
|---|---|---|---|---|---|---|---|---|
| 8 | 50 | 1 | 7 | 13.1 | 1.2:1 | 0.13 | 0.0002 | 0.0003 |
| 9 | 50 | 5 | 7 | 13.1 | 1.2:1 | 0.13 | None detected | 0.0004 |

Example 2E

This Example was performed according to the process described in Example 2A. However, in this Example 9.5 g of wet oxycodone HCl (0.02 moles; 0.13-0.14% by weight 14-hydroxycodeinone (14-OHC) impurity) was mixed with about 39.7 g of $H_2O$ and about 55.6 g of 6 wt. % $SO_2/H_2O$ solution. The mixture was heated to either 10° C. or 50° C. Next, the pH was adjusted to about 7 using ammonium hydroxide.

The resulting mixture was allowed to react for either 1 hour or 5 hours. At the end of the desired reaction time, the solution was adjusted to a pH of 8.8-9.8 with about 2.0-2.5 g of concentrated ammonium hydroxide and stirred for about 30 minutes. The solids were filtered and washed with about 30.6 g of $H_2O$ and dried. The 14-hydroxycodeinone (14-OHC) content in the resulting oxycodone base was measured, as was the 14-hydroxycodeinone (14-OHC) content in the oxycodone HCl salt formed by the method described in the preceding example. The results and reaction conditions in the various trials are illustrated in Table 6.

sulfuric acid was added as the pressure was decreased to about 0.11 atm and the solution temperature was increased to about 50-55° C.

The solution was then cooled to about 30° C. and the solution pH adjusted to about 8.5-10 with concentrated ammonium hydroxide. The solution was stirred for about 30 minutes and filtered. The solids were filtered and washed with about 2000 g of $H_2O$ and dried. The 14-hydroxycodeinone (14-OHC) content in the resulting oxycodone base was measured, as was the 14-hydroxycodeinone (14-OHC) content in the oxycodone HCl salt formed by the method described in the preceding example. The results and reaction conditions are illustrated in Table 7.

TABLE 6

| Trial | Temperature (° C.) | Time (hr.) | pH | Concentration (g $H_2O$ per g Oxycodone HCl) | Molar Ratio of $SO_2$ to Oxycodone HCl | Initial 14-OHC content (% by wt.) | Final 14-OHC content | |
|---|---|---|---|---|---|---|---|---|
| | | | | | | | Oxycodone base (% by wt.) | Oxycodone HCl (% by wt.) |
| 10 | 50 | 1 | 7 | 12.3 | 2.4:1 | 0.13 | None detected | 0.0004 |
| 11 | 50 | 5 | 7 | 12.3 | 2.4:1 | 0.13 | None detected | 0.0004 |
| 12 | 10 | 5 | 7 | 12.3 | 2.4:1 | 0.13 | 0.0008 | Not tested |

Example 2F

To a 22 L, 3 neck round bottom flask equipped with a mechanical stirrer, $N_2$ inlet, and thermocouple for temperature control was added 1840 g of wet oxycodone HCl (4.27 moles, 0.13% by weight 14-hydroxycodeinone (14-OHC) impurity). Next, with mixing 2706 g of $H_2O$ and 7717 g of 6.4 wt. % $SO_2/H_2O$ solution was added. The resulting mixture was heated to about 40° C. and the solution pH was adjusted to about 7 using concentrated ammonium hydroxide. The mixture was stirred for about 5 hours.

After about 5 hours, the solution was adjusted to a pH of about 1.7 with the addition of 293.0 g concentrated sulfuric acid (96-98%). The pressure was slowly reduced to about 0.26 atm to facilitate the distillation/removal of unreacted $SO_2$. As the distillation progressed, 23.4 g of concentrated

TABLE 7

| Trial | Temperature (° C.) | Time (hr.) | pH | Concentration (g $H_2O$ per g Oxycodone HCl) | Molar Ratio of $SO_2$ to Oxycodone HCl | Initial 14-OHC content (% by wt.) | Final 14-OHC content | |
|---|---|---|---|---|---|---|---|---|
| | | | | | | | Oxycodone base (% by wt.) | Oxycodone HCl (% by wt.) |
| 13 | 40 | 5 | 7 | 6.6 | 1.8:1 | 0.13 | 0.0001 | 0.0005 |

Example 2G

To a 50 ml, 3 neck round bottom flask equipped with a mechanical stirrer, $N_2$ inlet, and thermocouple for temperature control was added 3.33 g of oxycodone HCl (0.0095 moles; 0.2% by weight 14-hydroxycodeinone (14-OHC) impurity). Next, with mixing 33.3 g of $H_2O$ and 0.83 g of sodium bisulfite was added. The resulting mixture was heated to about 30° C. and the solution pH was adjusted to about 7 with ammonium hydroxide. The mixture was stirred for about 15 hours. The pH of the mixture was then adjusted to about 8.8-9.8 with concentrated ammonium hydroxide and stirred for about 60 minutes. The precipitated oxycodone base was then filtered from the mother liquor, washed with about 10.0 g of $H_2O$, and dried. The 14-hydroxycodeinone (14-OHC) content in the resulting oxycodone base was measured, as was the 14-hydroxycodeinone (14-OHC) content in the oxycodone HCl salt formed by the method described in the preceding example. The results and reaction conditions in the various trials are illustrated in Table 8.

TABLE 8

| Trial | Temperature (°C.) | Time (hr.) | pH | Concentration (g H$_2$O per g Oxycodone HCl) | Molar Ratio of SO$_2$ to Oxycodone HCl | Initial 14-OHC content (% by wt.) | Final 14-OHC content | |
|---|---|---|---|---|---|---|---|---|
| | | | | | | | Oxycodone base (% by wt.) | Oxycodone HCl (% by wt.) |
| 14 | 30 | 15 | 7 | 10 | 0.84:1 | 0.2 | 0.0004 | 0.0004 |

EXAMPLE 3

In this Example, an oxymorphone HCl sample was treated with a sulfur-containing compound according to the processes described herein.

To a 250 ml, 3 neck round bottom flask equipped with a mechanical stirrer, N$_2$ inlet, and thermocouple for temperature control was added 150 g H$_2$O and 15 g oxymorphone HCl sample (0.044 moles; 0.3-0.5% by weight 14-hydroxymorphinone (14-OHM) impurity). Next, 7.5 g of sodium bisulfite (NaHSO$_3$) was added. The pH was then adjusted to about 7 with concentrated ammonium hydroxide, and the resulting mixture was stirred at 23° C. for about 16 hours.

After about 16 hours, the pH was adjusted to about 8.8-9.8 with ammonium hydroxide and the solution was cooled to about 20° C. The precipitated oxymorphone base was filtered, washed with water (about 45 g), and dried for 4 hours at 65° C.

The oxymorphone base sample was analyzed using the methods described above, and the sample contained no detectable amount of 14-hydroxymorphinone or 14-hydroxycodeinone. This experiment was repeated using a 6 wt. % SO$_2$/H$_2$O solution in place of sodium bisulfite and similar results were obtained.

EXAMPLE 4

In this Example, oxycodone base was treated with a thiol according to the processes described herein.

To a 25 ml, 3 neck round bottom flask equipped with a mechanical stirrer, N$_2$ inlet, and thermocouple for temperature control was added 3.0 g oxycodone base (0.01 motes; 0.3-0.5% by weight 14-hydroxycodeinone (14-OHC) impurity). Next, 18 g of chloroform was added, and the mixture was stirred at 70° C. until the oxycodone base was dissolved. After the mixture was substantially homogenous, 1.5 g of benzenethiol was added to the mixture with stirring.

After about 16 hours, a sample was analyzed using the methods described in the preceding examples. HPLC area percent analysis indicated a 14-hydroxycodeinone level of less than about 0.0022%.

What is claimed is:

1. A hydrochloride salt of oxymorphone comprising less than 0.001% of 14-hydroxymorphinone.

2. The hydrochloride salt of claim 1 comprising less than 0.0005% of 14-hydroxymorphinone.

3. A pharmaceutical acceptable form comprising the oxymorphone hydrochloride according to claim 1.

4. A hydrochloride salt of a morphinan-6-one compound corresponding to Formula (2):

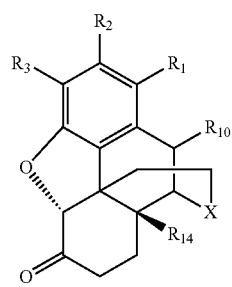

(2)

comprising less than 0.001% measured by HPLC of an α,β-unsaturated ketone compound corresponding to Formula (3):

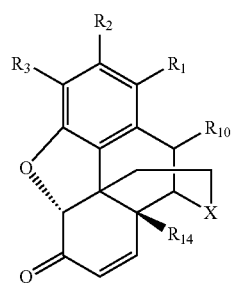

(3)

wherein the morphinan-6-one compound is oxymorphone and wherein X is —N(R$_{17}$)—;

R$_1$ and R$_2$ are hydrogen;

R$_3$ is hydroxy;

R$_{10}$ is hydrogen;

R$_{14}$ is hydroxy; and

R$_{17}$ is methyl.

5. The hydrochloride salt of claim 4 comprising less than 0.0005% of 14-hydroxymorphinone.

6. A pharmaceutical formulation comprising the oxymorphone hydrochloride according to claim 4.

* * * * *